United States Patent
Lui et al.

(10) Patent No.: US 11,331,130 B1
(45) Date of Patent: May 17, 2022

(54) STERNAL CLOSURE SYSTEMS AND METHODS OF USE THEREOF

(71) Applicant: DEPUY SYNTHES PRODUCTS, INC., Raynham, MA (US)

(72) Inventors: Eric Lui, Royersford, PA (US); Evangelos Theodorou, Derendingen (CH); Christopher Keegan, Hatboro, PA (US)

(73) Assignee: Depuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 17/117,693

(22) Filed: Dec. 10, 2020

(51) Int. Cl.
*A61B 17/80* (2006.01)
*A61B 17/064* (2006.01)

(52) U.S. Cl.
CPC ...... *A61B 17/8076* (2013.01); *A61B 17/0642* (2013.01); *A61B 17/8004* (2013.01); *A61B 17/808* (2013.01); *A61B 17/809* (2013.01)

(58) Field of Classification Search
CPC . A61B 17/0642; A61B 17/80; A61B 17/8004; A61B 17/8061; A61B 17/8076; A61B 17/809
See application file for complete search history.

(56) References Cited

U.S. PATENT DOCUMENTS

| | | | |
|---|---|---|---|
| 4,906,189 A | 3/1990 | Knapp | |
| 5,246,443 A | 9/1993 | Mai | |
| 5,662,655 A * | 9/1997 | Laboureau | A61B 17/0642 606/75 |
| 5,779,707 A | 7/1998 | Bertholet et al. | |
| 5,947,999 A * | 9/1999 | Groiso | A61F 2/0811 606/219 |
| 5,993,476 A | 11/1999 | Groiso | |
| 6,616,669 B2 | 9/2003 | Ogilivie et al. | |
| 6,773,437 B2 | 8/2004 | Ogilivie et al. | |
| 7,156,847 B2 | 1/2007 | Abramson | |
| 7,481,832 B1 | 1/2009 | Meridew et al. | |
| 7,871,411 B2 * | 1/2011 | Grevious | A61B 17/8061 606/60 |

(Continued)

FOREIGN PATENT DOCUMENTS

| | | |
|---|---|---|
| KR | 101037957 B1 | 5/2011 |
| WO | 1992017122 A2 | 10/1992 |

(Continued)

*Primary Examiner* — Larry E Waggle, Jr.
(74) *Attorney, Agent, or Firm* — Christopher L. Makay

(57) ABSTRACT

A sternal closure system for closing an opening in a sternum includes an implant and a plate pair comprised of first and second plates. The first and second plates secure with the sternum across the opening. The implant, in an insertion shape, inserts through the first and second plates and into the sternum across the opening, and then, upon a movement toward a natural shape, holds the opening closed while interconnecting the first and second plates. The sternal closure system alternatively includes an implant with a bridge having first and second apertures and first and second legs extending from the bridge. The implant, in an insertion shape, inserts into the sternum across the opening, and then, upon a movement toward a natural shape, holds the opening in the sternum closed. The implant, at the first and second apertures, receives fixation devices therethrough that engage the sternum.

26 Claims, 18 Drawing Sheets

(56) References Cited

U.S. PATENT DOCUMENTS

| | | |
|---|---|---|
| 8,425,572 B2 | 4/2013 | Grevious |
| 8,475,457 B2 * | 7/2013 | Shano ................ A61B 17/0642 606/75 |
| 8,579,938 B2 * | 11/2013 | Heinrich ............ A61B 17/0643 606/220 |
| D728,104 S | 4/2015 | Katchis et al. |
| 9,072,554 B2 | 7/2015 | Reynolds et al. |
| 9,173,690 B2 | 11/2015 | Winslow et al. |
| 9,393,058 B2 | 7/2016 | Aubin et al. |
| 9,532,820 B2 | 1/2017 | Weiner et al. |
| 9,649,108 B2 | 5/2017 | Weinstein et al. |
| 9,693,771 B2 | 7/2017 | Heinrich et al. |
| 9,801,671 B2 | 10/2017 | Knoepfle et al. |
| 10,080,599 B2 | 9/2018 | Caldera et al. |
| 10,292,743 B2 | 5/2019 | Taylor et al. |
| 10,307,193 B2 | 6/2019 | Garcia et al. |
| 10,433,888 B2 | 10/2019 | Hollis et al. |
| 2002/0013607 A1 * | 1/2002 | Lerner ................ A61B 17/1691 606/216 |
| 2003/0139746 A1 | 7/2003 | Groiso |
| 2008/0065153 A1 | 3/2008 | Allard et al. |
| 2008/0065154 A1 | 3/2008 | Allard et al. |
| 2011/0022049 A1 | 1/2011 | Huebner et al. |
| 2013/0231667 A1 | 9/2013 | Taylor et al. |
| 2017/0181779 A1 | 6/2017 | Leither et al. |
| 2017/0281157 A1 | 10/2017 | Hartdegen et al. |
| 2019/0223927 A1 | 7/2019 | Hollis et al. |
| 2019/0231404 A1 | 8/2019 | Taylor et al. |
| 2019/0374267 A1 * | 12/2019 | Madey ................ A61B 17/823 |
| 2020/0038076 A1 * | 2/2020 | Amis ................ A61B 17/8004 |

FOREIGN PATENT DOCUMENTS

| | | |
|---|---|---|
| WO | 2015176600 A1 | 11/2015 |
| WO | 2017207922 A1 | 12/2017 |

\* cited by examiner

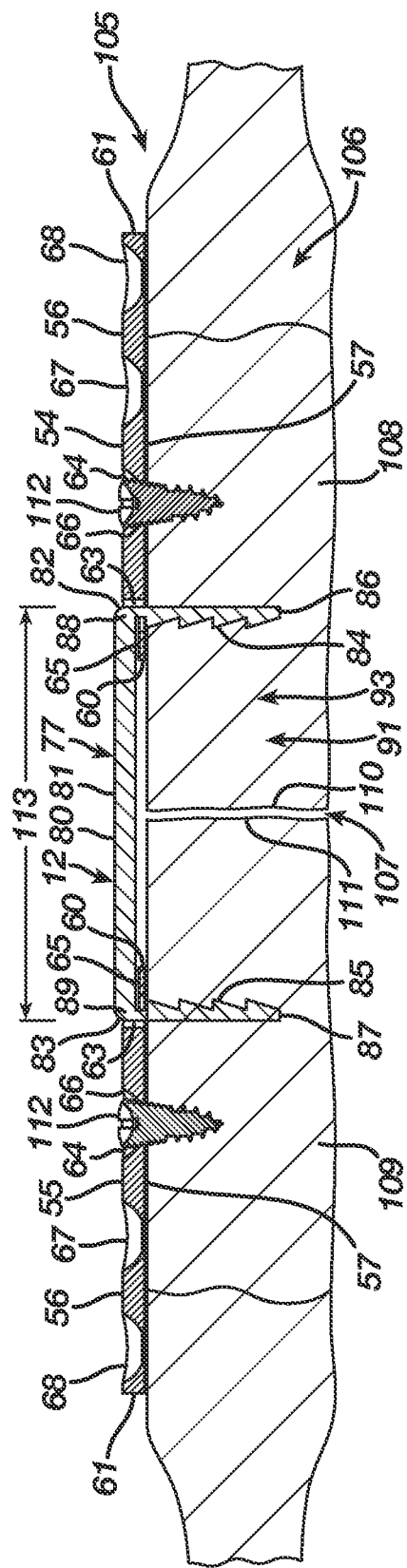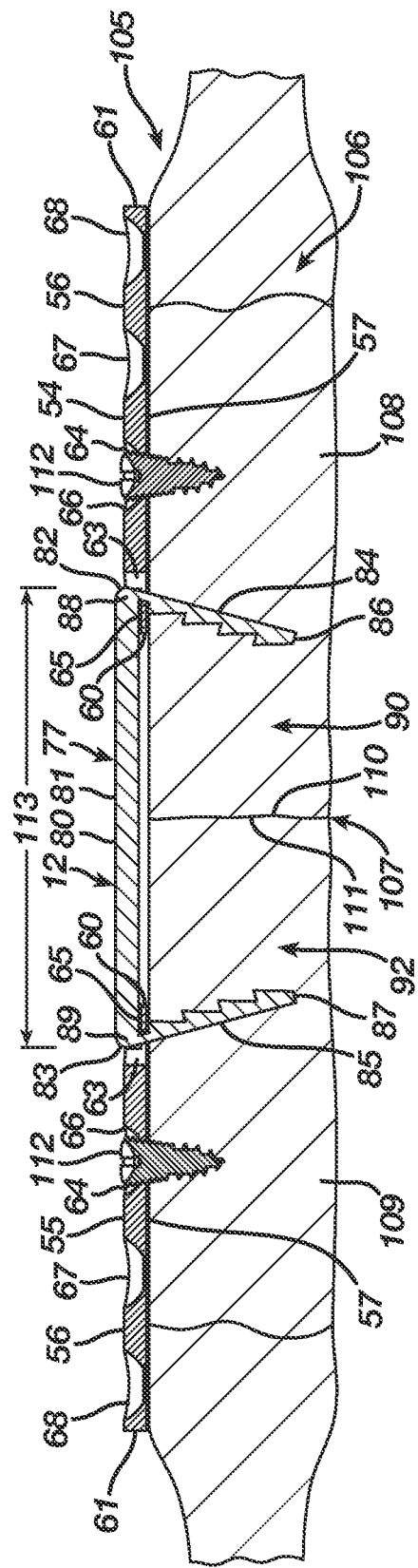

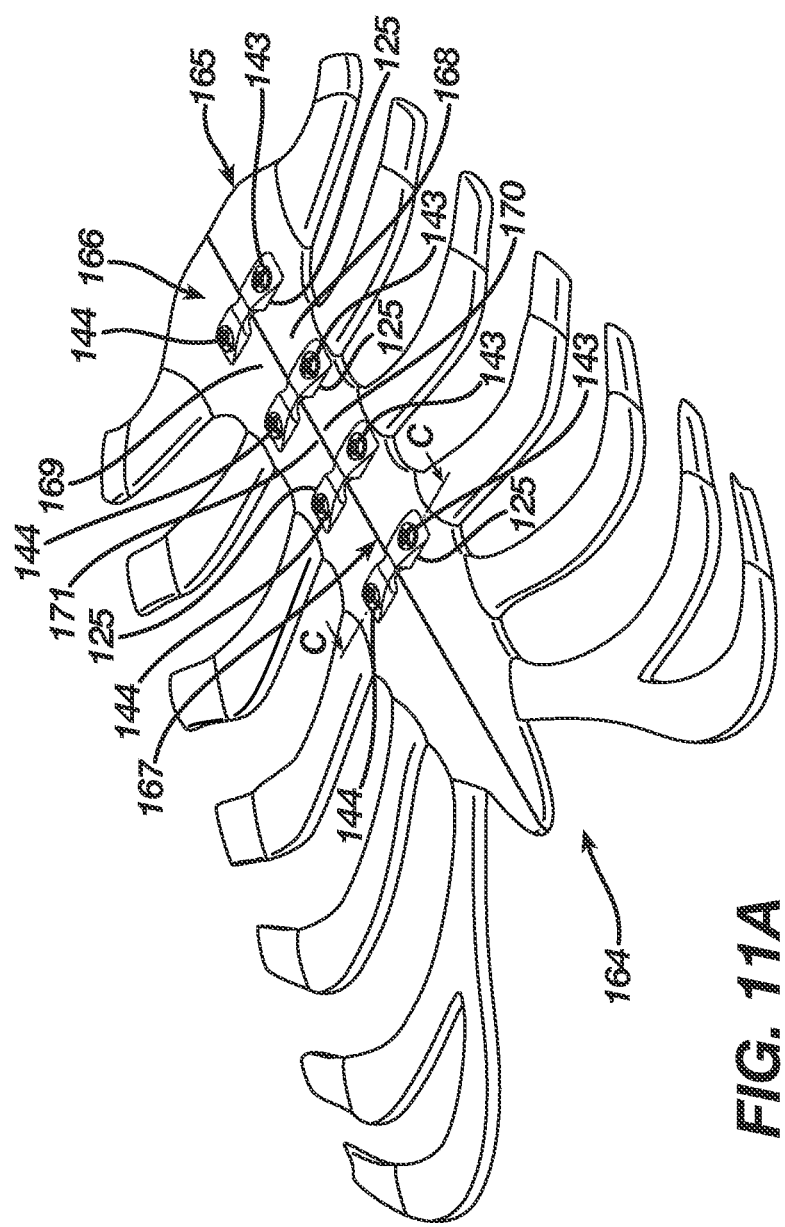

STERNAL CLOSURE SYSTEMS AND METHODS OF USE THEREOF

BACKGROUND OF THE INVENTION

1. Field of the Invention

The present invention relates to thoracic surgery and, more particularly, but not by way of limitation, to sternal closure systems utilized upon completion of a thoracic surgery.

2. Description of the Related Art

Thoracic surgery often involves access to a thoracic cavity through an opening created in a sternum. Upon completion of the thoracic surgery, the opening in the sternum must be closed. Surgical equipment and techniques currently available for sternal closure consist of cerclage and plate-based systems.

Cerclage includes maintaining the opening in the sternum closed while placing wires or loops about the sternum whereby the wires or loops hold the sternum closed along the opening created therein. Although cerclage achieves sternal closure, employing wires or loops to hold a sternum closed experiences certain disadvantages. During normal thoracic wall movement, including movement created through breathing, the wires or loops due to their relative inflexibility cut into the sternum, resulting in grooves developing in the sternum. The grooves not only weaken the sternum but also loosen the wires or loops such that a potential for the sternum to re-open exists.

Plate-based systems include maintaining the opening in the sternum closed while securing one or more plates via screws to the sternum and/or ribs whereby the plates, which span the sternum across the opening created therein, hold the sternum closed. Although plate-based systems achieve sternal closure, employing screw fixated plates to hold a sternum closed experiences certain disadvantages. During normal thoracic wall movement, including movement created through breathing, the screws securing the plates slacken due to the relative inflexibility of the plates, resulting in loose plates and a possible shifting thereof relative to the sternum and a potential for the sternum to re-open. Moreover, in the event a later acute re-entry into a thoracic cavity becomes necessary, screw fixated plates are difficult and time consuming to remove, creating a potential life-threatening situation.

Accordingly, sternal closure systems that achieve a desired sternal closure while remaining flexible to account for thoracic wall movement and further are quickly removable in the event acute re-entry through a sternum becomes necessary will provide improvements in sternal closure.

SUMMARY OF THE INVENTION

In accordance with the present invention, a sternal closure system for closing an opening in a sternum of a thoracic wall includes a plurality of implants and a plurality of plate pairs comprised of a first plate and a second plate. While the sternal closure system includes a plurality of implants and plate pairs, the sternal closure system is operative to close the opening in the sternum using one implant and one plate pair comprised of a first plate and a second plate. The implant moves between a natural shape and an insertion shape. The first plate, which receives the implant therethrough, secures with the sternum adjacent a first side of the opening. The second plate, which receives the implant therethrough, secures with the sternum adjacent a second side of the opening. The implant, when positioned in the insertion shape, inserts through the first plate and the second plate and into the sternum across the opening. The implant, upon a movement thereof from the insertion shape toward the natural shape, holds the opening in the sternum closed while interconnecting the first plate and the second plate.

The implant includes a bridge having a length and with a first end and a second end. The implant further includes a first leg extending from the bridge and a second leg extending from the bridge. The first leg and the second leg reside in a natural position at a first distance when the implant is positioned in the natural shape. The first leg and the second leg reside in an insertion position at a second distance when the implant is positioned in the insertion shape.

The first plate includes a first end and a second end, a first side and a second side, a first aperture extending through the first plate at the first end, and a second aperture adjacent the first aperture extending through the first plate. Likewise, the second plate includes a first end and a second end, a first side and a second side, a first aperture extending through the second plate at the first end, and a second aperture adjacent the first aperture extending through the second plate.

In a first embodiment, the first aperture and the second aperture of the first plate and the second plate are configured to receive therethrough either a fixation device or one of the first leg and the second leg of the implant. The first plate and the second plate include a first slot extending from the first aperture to the first side and a second slot extending from the second aperture to the first side. The first and second slots are configured to receive therein the bridge of the implant at either the first end or the second end of the bridge. The first and second slots permit seating of the implant within the first plate or the second plate. The first plate and the second plate include a first countersink at the first aperture and a second countersink at the second aperture. The first and second countersinks are configured to receive therein a fixation device in order to permit seating of the fixation device within either the first plate or the second plate.

The first plate secures with the sternum adjacent the first side of the opening using a fixation device inserted through the first aperture and into the sternum. Similarly, the second plate secures with the sternum adjacent the second side of the opening using a fixation device inserted through the first aperture and into the sternum. The second aperture of the first plate and the second aperture of the second plate align and are separated across the opening by a distance substantially equal to the second distance of the first leg and the second leg in the insertion position. Moreover, the first plate and the second plate are oriented substantially parallel whereby the second slot of the first plate aligns with the second slot of the second plate. With the implant positioned in the insertion shape whereby the first leg and the second leg reside in the insertion position at the second distance, the first leg of the implant inserts through the second aperture of the first plate and into the sternum and the second leg of the implant inserts through the second aperture of the second plate and into the sternum such that the bridge spans the opening. The first leg and the second leg insert into the sternum until the bridge of the implant seats at the first end in the second slot of the first plate and at the second end in the second slot of the second plate. The implant, upon a movement thereof from the insertion shape toward the natural shape, holds the opening in the sternum closed while the first leg engages the first plate and the second leg engages the second plate such that the implant interconnects the first plate and the second plate.

The first plate and the second plate include a third aperture adjacent the second aperture that extends through the first plate and the second plate. The third aperture is configured to receive therethrough either a fixation device and one of the first leg and the second leg of the implant. When securing the first plate with the sternum adjacent the first side of the opening, fixation devices insert through the first aperture and the third aperture and into the sternum. Likewise, when securing the second plate with the sternum adjacent the second side of the opening, fixation devices insert through the first aperture and the third aperture and into the sternum.

In a second embodiment, the first aperture of the first plate and the second plate is configured to receive therethrough one of the first leg and the second leg of the implant, whereas the second aperture of the first plate and the second plate is configured to receive therethrough a fixation device. The first plate and the second plate include a slot extending from the first aperture to the first end. The slot is configured to receive therein the bridge of the implant at either the first end or the second end of the bridge. The slot permits seating of the implant within the first plate and the second plate. The first plate and the second plate include a countersink at the second aperture. The countersink is configured to receive therein a fixation device in order to permit seating of the fixation device within either the first plate or the second plate.

The first plate secures with the sternum adjacent the first side of the opening using a fixation device inserted through the second aperture and into the sternum. Similarly, the second plate secures with the sternum adjacent the second side of the opening using a fixation device inserted through the second aperture and into the sternum. The first aperture of the first plate and the first aperture of the second plate align and are separated across the opening by a distance substantially equal to the second distance of the first leg and the second leg in the insertion position. Moreover, the first plate and the second plate are oriented substantially perpendicular whereby the slot of the first plate aligns with the slot of the second plate. With the implant positioned in the insertion shape whereby the first leg and the second leg reside in the insertion position at the second distance, the first leg of the implant inserts through the first aperture of the first plate and into the sternum and the second leg of the implant inserts through the first aperture of the second plate and into the sternum such that the bridge of the implant spans the opening. The first leg and the second leg insert into the sternum until the bridge of the implant seats at the first end in the slot of the first plate and at the second end in the slot of the second plate. The implant, upon a movement thereof from the insertion shape toward the natural shape, holds the opening in the sternum closed while the first leg engages the first plate and the second leg engages the second plate such that the implant interconnects the first plate and the second plate.

The first plate and the second plate include a third aperture adjacent the second aperture that extends through the first plate and the second plate. The third aperture is configured to receive therethrough a fixation device. When securing the first plate with the sternum adjacent the first side of the opening, a fixation device inserts through the second aperture and into the sternum and a fixation device inserts through the third aperture and into either the sternum or a rib of the thoracic wall. Likewise, when securing the second plate with the sternum adjacent the second side of the opening, a fixation device inserts through the second aperture and into the sternum and a fixation device inserts through the third aperture and into either the sternum or a rib of the thoracic wall.

The sternal closure system alternatively in a third embodiment includes a plurality of implants with each implant being moveable between a natural shape and an insertion shape. The plurality of implants, in the insertion shape, inserts into the sternum across the opening, and then, upon a movement toward a natural shape, the plurality of implants holds the opening in the sternum closed. While the sternal closure system includes a plurality of implants, the sternal closure system is operative to close the opening in the sternum using one implant or at least a first implant and a second implant.

The first implant and the second implant each include a bridge having a length and with a first end, a second end, and a central axis therebetween, a first leg extending from the bridge at the first end, and a second leg extending from the bridge at the second end. The bridge is deformable between a natural form and an insertion form that transitions the first implant and the second implant between the natural shape and the insertion shape. When the bridge is positioned in the natural form, the first leg and the second leg reside in a natural position with the first leg and the second leg spaced apart at a first distance. Conversely, when the bridge is positioned in the insertion form, the first leg and the second leg reside in an insertion position with the first leg and the second leg spaced apart at a second distance greater than the first distance. The bridge includes a first aperture therethrough positioned from the central axis lengthwise along the bridge to a location adjacent the first leg. The first aperture receives a fixation device that secures the bridge adjacent the first end with the sternum. Likewise, the bridge includes a second aperture therethrough positioned from the central axis lengthwise along the bridge to a location adjacent the second leg. The second aperture receives a fixation device that secures the bridge adjacent the second end with the sternum. The bridge further includes a groove at the central axis. The groove reduces a cross-section of the bridge and facilitates a cutting of the bridge that re-opens the opening in the sternum.

The first implant, when positioned in the insertion shape with the bridge in the insertion form and the first leg and the second leg in the insertion position at the second distance, secures with the sternum across the opening at a first location. More particularly, the first leg inserts into the sternum adjacent a first side of the opening, the second leg inserts into the sternum adjacent a second side of the opening, and the bridge spans the opening. The first implant, upon a movement thereof from the insertion shape toward the natural shape with the bridge moving toward the natural form and the first leg and the second leg moving toward the natural position, holds the opening in the sternum closed at the first location. The movement of the bridge toward the natural form and the first leg and the second leg toward the natural position facilitates an engagement of the first leg with the sternum at the first side of the opening, an engagement of the second leg with the sternum at the second side of the opening, and a compression of the sternum at the first location that holds the opening closed. The first aperture receives a fixation device therethrough that engages the sternum at the first side of the opening in order to secure the bridge adjacent the first end with the sternum. The second aperture receives a fixation device therethrough that engages the sternum at the second side of the opening in order to secure the bridge adjacent the second end with the sternum.

Similarly, the second implant, when positioned in the insertion shape with the bridge in the insertion form and the first leg and the second leg in the insertion position at the second distance, secures with the sternum across the opening at a second location. The first leg inserts into the sternum adjacent a first side of the opening, the second leg inserts into the sternum adjacent a second side of the opening, and the bridge spans the opening. The second implant, upon a movement thereof from the insertion shape toward the natural shape with the bridge moving toward the natural form and the first leg and the second leg moving toward the natural position, holds the opening in the sternum closed at the second location. The movement of the bridge toward the natural form and the first leg and the second leg toward the natural position facilitates an engagement of the first leg with the sternum at the first side of the opening, an engagement of the second leg with the sternum at the second side of the opening, and a compression of the sternum at the second location that holds the opening closed. The first aperture receives a fixation device therethrough that engages the sternum at the first side of the opening to secure the bridge adjacent the first end with the sternum. The second aperture receives a fixation device therethrough that engages the sternum at the second side of the opening to secure the bridge adjacent the second end with the sternum.

A method for a sternal closure system adapted for closing an opening in a sternum of a thoracic wall includes the following steps. An implant is constrained in the insertion shape. A first plate secures with the sternum adjacent a first side of the opening, while a second plate securing with the sternum adjacent a second side of the opening. An aperture of the first plate and an aperture of the second plate are aligned and separated across the opening by a distance substantially equal to a distance between a first leg and a second leg when the implant resides in the insertion shape. The first leg of the implant inserts through the aperture of the first plate into the sternum, the second leg of the implant inserts through the aperture of the second plate into the sternum, and a bridge of the implant spans the opening. The implant is released such that, upon a movement of the implant from the insertion shape toward the natural shape, the implant holds the opening in the sternum closed while the first leg engages the first plate and the second leg engages the second plate in order for the implant to interconnect the first plate and the second plate.

A method for a sternal closure system adapted for closing an opening in a sternum of a thoracic wall alternatively includes the following steps. A first implant and a second implant are constrained in the insertion shape. A first leg of the first implant inserts into the sternum adjacent a first side of the opening, a second leg of the first implant inserts into the sternum adjacent a second side of the opening, and a bridge of the first implant spans the opening at a first location. The first implant is released such that, upon a movement of the first implant from the insertion shape toward the natural shape, the first leg engages with the sternum at the first side of the opening, the second leg engages with the sternum at the second side of the opening, and the first implant compresses the sternum at the first location thereby holding the opening closed. A fixation device inserts through a first aperture of the bridge for the first implant and into the sternum at the first side of the opening thereby securing the bridge with the sternum. A fixation device inserts through a second aperture of the bridge for the first implant and into the sternum at the second side of the opening thereby securing the bridge with the sternum. Similarly, a first leg of the second implant inserts into the sternum adjacent a first side of the opening, a second leg of the second implant inserts into the sternum adjacent a second side of the opening, and a bridge of the second implant spans the opening at a second location. The second implant is released such that, upon a movement of the second implant from the insertion shape toward the natural shape, the first leg engages with the sternum at the first side of the opening, the second leg engages with the sternum at the second side of the opening, and the second implant compresses the sternum at the second location thereby holding the opening closed. A fixation device inserts through a first aperture of the bridge for the second implant and into the sternum at the first side of the opening thereby securing the bridge with the sternum. A fixation device inserts through a second aperture of the bridge for the second implant and into the sternum at the second side of the opening thereby securing the bridge with the sternum.

It is therefore an object of the present invention to provide sternal closure systems that achieve a desired sternal closure while remaining flexible to account for thoracic wall movement.

It is another object of the present invention to provide sternal closure systems that in view of their flexibility prevent a movement of the sternal closure systems about a sternum, a loosening of the sternal closure systems relative to the sternum, or a dislodgement of the sternal closure systems from the sternum that causes a re-opening of the sternum.

It is a further object of the present invention to provide sternal closure systems that are quickly removable in the event acute re-entry through a sternum becomes necessary.

Still other objects, features, and advantages of the present invention will become evident to those of ordinary skill in the art in light of the following. Also, it should be understood that the scope of this invention is intended to be broad, and any combination of any subset of the features, elements, or steps described herein is part of the intended scope of the invention.

BRIEF DESCRIPTION OF THE DRAWINGS

FIG. 8B is a cross-sectional view taken along lines B-B of FIG. 8A illustrating the sternal closure system according to the second embodiment as utilized in closing a sternum whereby the implant resides in its insertion shape.

FIG. 8C is a cross-sectional view taken along lines B-B of FIG. 8A illustrating the sternal closure system according to the second embodiment as utilized in closing a sternum whereby the implant attempts transition to its natural shape.

FIG. 11A is an isometric view illustrating the sternal closure system according to the third embodiment as utilized in closing a sternum.

DETAILED DESCRIPTION OF THE PREFERRED EMBODIMENTS

Figure 1:
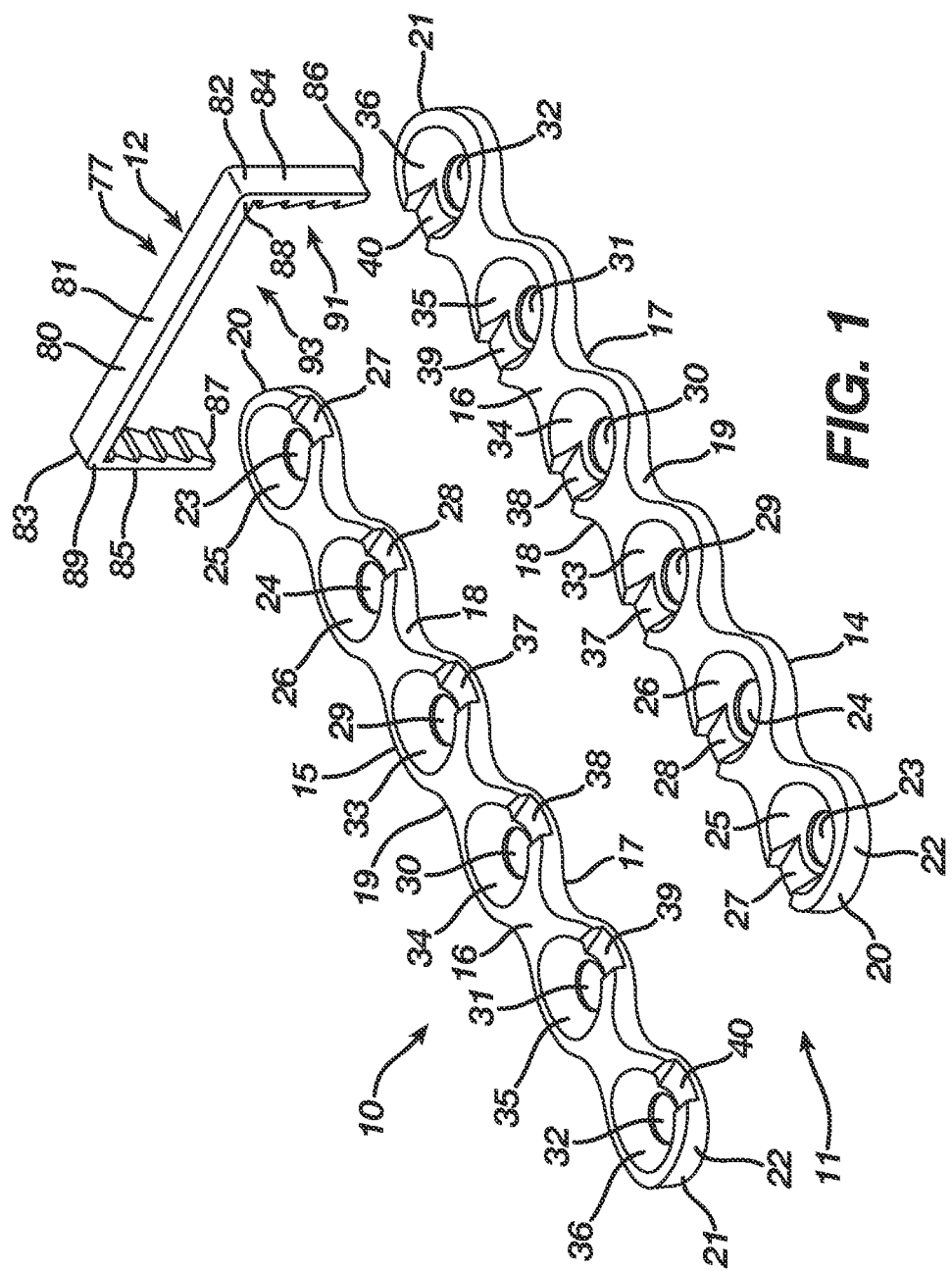
FIG. 1 is an isometric view illustrating a sternal closure system according to a first embodiment.
Figure 2A:
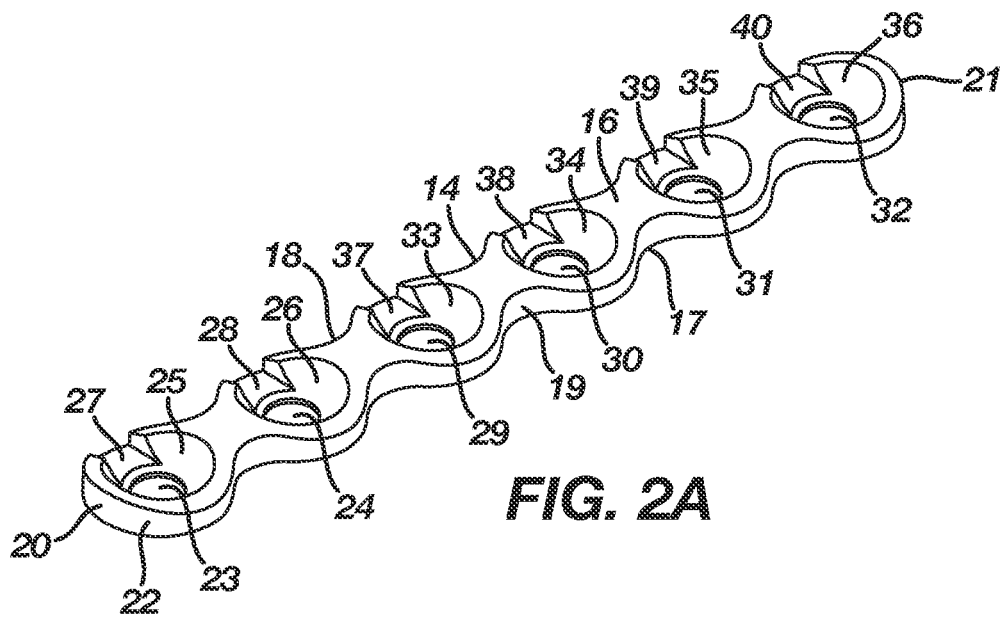
FIGS. 2A and 2B are isometric views illustrating a plate for the sternal closure system according to the first embodiment.
Figure 2B:
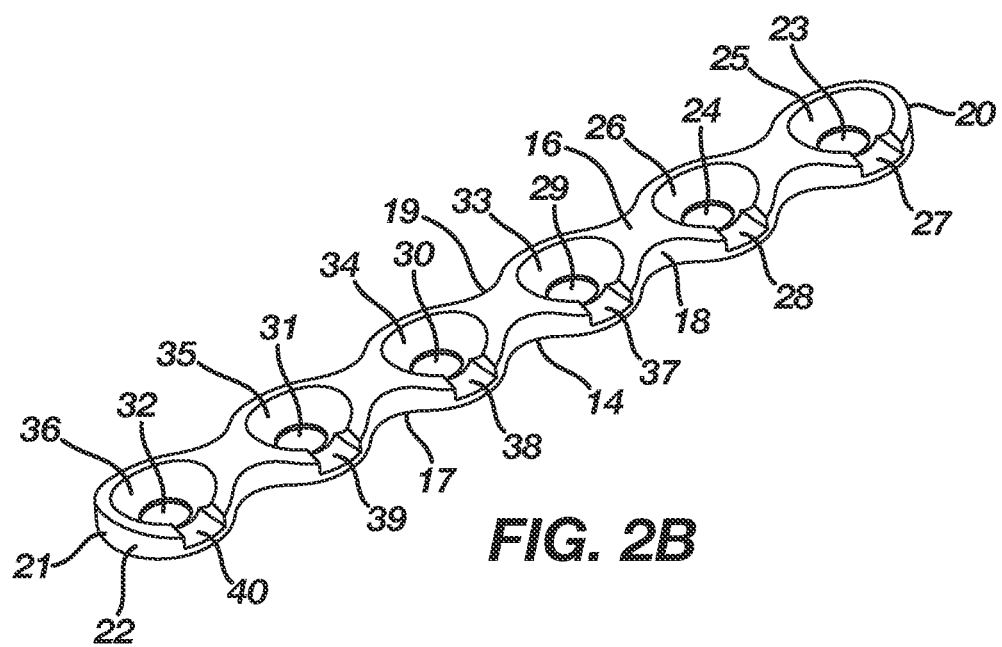
Figure 2C:
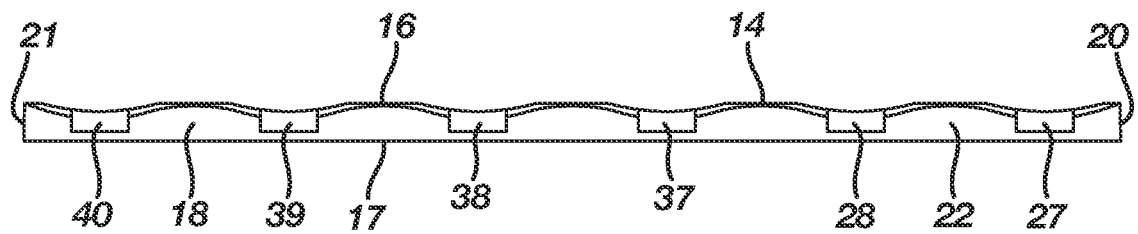
FIG. 2C is a side view taken from the front illustrating the plate for the sternal closure system according to the first embodiment.
Figure 2D:
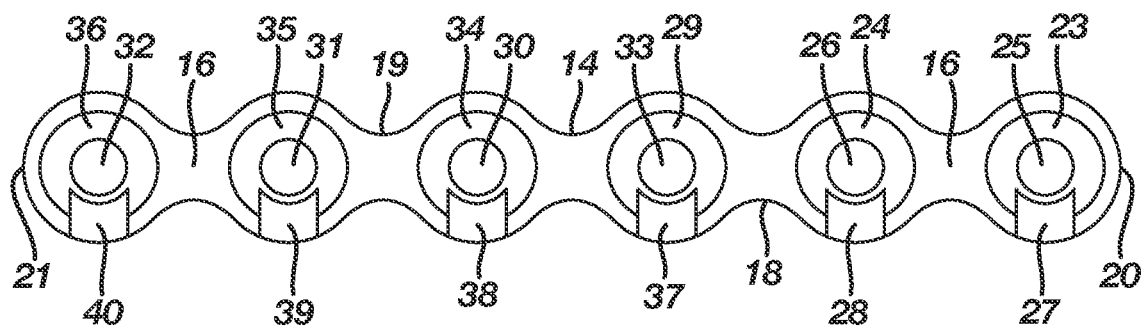
FIG. 2D is a top view illustrating the plate for the sternal closure system according to the first embodiment.
Figure 2E:
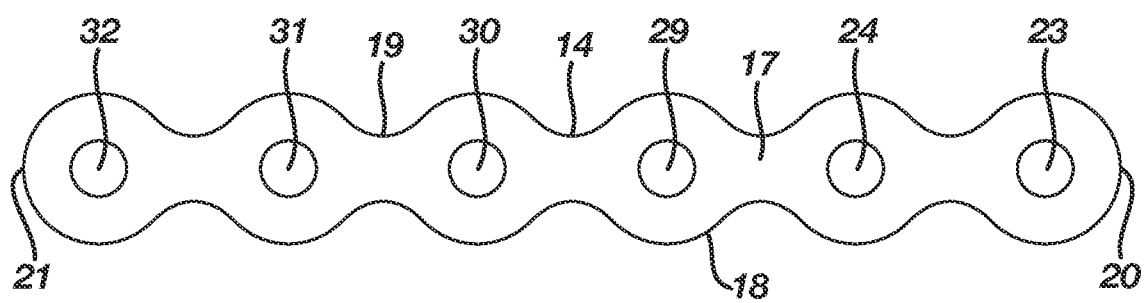
FIG. 2E is a bottom view illustrating the plate for the sternal closure system according to the first embodiment.
Figure 3:
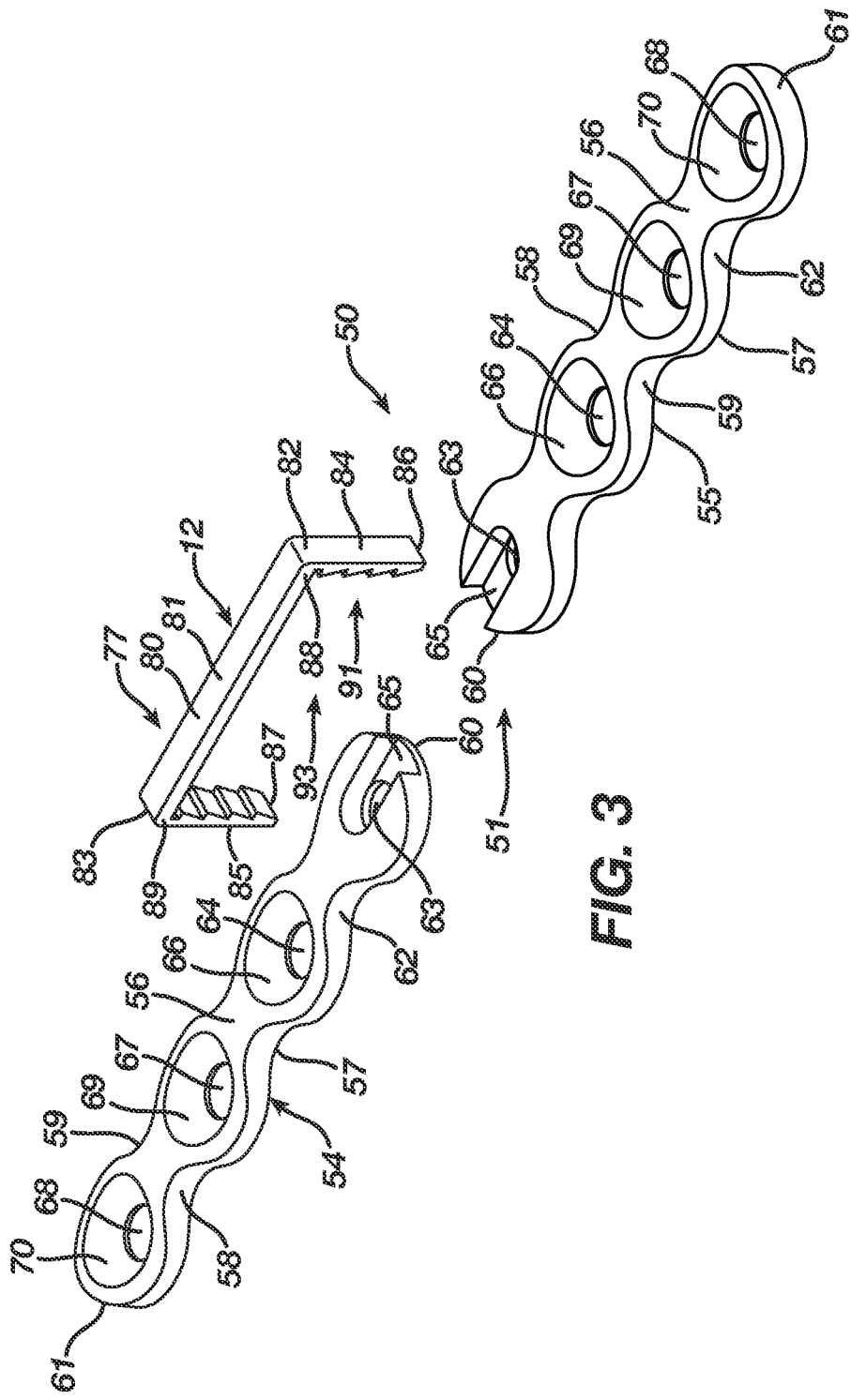
FIG. 3 is an isometric view illustrating a sternal closure system according to a second embodiment.
Figure 4A:
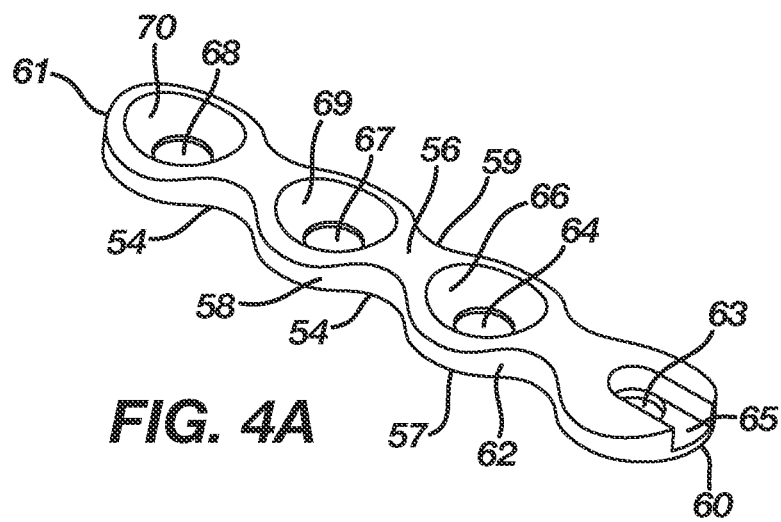
FIG. 4A is an isometric view illustrating a plate for the sternal closure system according to the second embodiment.
Figure 4B:
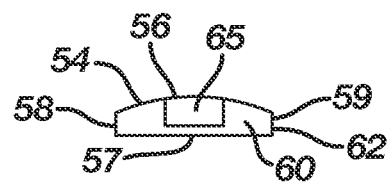
FIG. 4B is an end view taken from the front illustrating the plate for the sternal closure system according to the second embodiment.
Figure 4C:
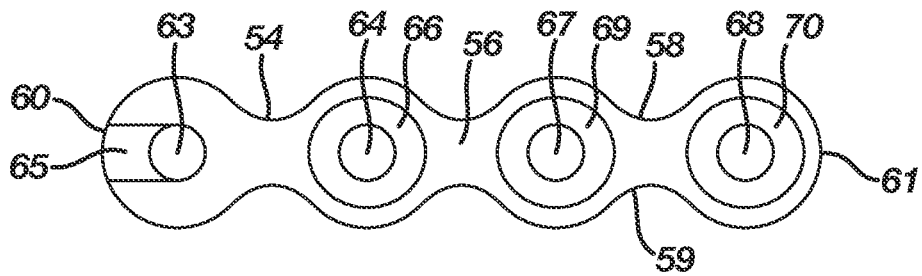
FIG. 4C is a top view illustrating the plate for the sternal closure system according to the second embodiment.
Figure 4D:
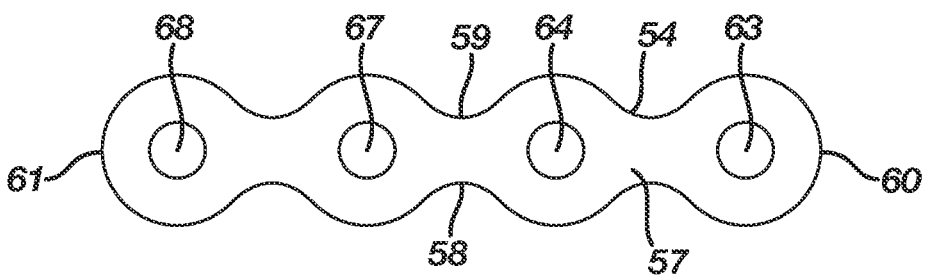
FIG. 4D is a bottom view illustrating the plate for the sternal closure system according to the second embodiment.

As required, detailed embodiments of the present invention are disclosed herein; however, it is to be understood that the disclosed embodiments are merely exemplary of the invention, which may be embodied in various forms. It is further to be understood that the figures are not necessarily to scale, and some features may be exaggerated to show details of particular components or steps.

As illustrated in FIGS. 1-2E and 5A-6B, a sternal closure system 10 according to a first embodiment includes one or more plate pairs 11 and one or more implants 12. A plate pair 11 in the first embodiment includes a first plate 14 and a second plate 15.

The first plate 14 with reference to FIGS. 2A-2E exhibits a three-dimensional form having a length, width, and height, and, in particular, the first plate 14 includes an upper surface 16 and a lower surface 17 with first and second sides 18 and 19 and first and second ends 20 and 21 therebetween. The upper surface 16 and the lower surface 17 define a height 22 that provides strength to the first plate 14 while a contouring of the upper surface 16 presents the first plate 14 with a lowest possible profile. The lower surface 17 is flat in order for the first plate 14 at its lower surface 17 to seat flush atop a thoracic wall. The first plate 14 in the first embodiment is any suitable biocompatible metal, such as, for example, titanium.

The first plate 14 includes at least a first aperture 23 at the first end 20 extending therethrough from the upper surface 16 to the lower surface 17 and a second aperture 24 adjacent the first aperture 23 extending therethrough from the upper surface 16 to the lower surface 17. The first plate 14 includes the first and second apertures 23 and 24 in order for the first plate 14 to receive therethrough either a fixation device or the implant 12. In the first embodiment, the fixation device is any suitable biocompatible metal screw, such as, for example, titanium, including a non-locking bone screw, a locking bone screw, and a self-tapping bone screw. The first plate 14 at the upper surface 16 and the first aperture 23 is configured to receive therein a screw through a countersink 25 that permits the screw to seat flush in the first plate 14. The first plate 14 at the upper surface 16 and the first aperture 23 is configured to receive therein the implant 12 through a slot 27 extending from the first aperture 23 to the first side 18 of the first plate 14 whereby the slot 27 permits the implant 12 to seat flush in the first plate 14. The first plate 14 at the upper surface 16 and the second aperture 24, similar to the first aperture 23, includes a countersink 26 and a slot 28 that are identical to the countersink 25 and the slot 27.

While a securing of the first plate 14 to a thoracic wall and a closing of an opening through a sternum requires only the first and second apertures 23 and 24, the first plate 14 in the first embodiment includes an aperture 29 adjacent the second aperture 24 and apertures 30-32 extending along the first plate 14 to the second end 21 thereof, whereby the apertures 29-32 are similar to the first and second apertures 23 and 24. The first plate 14 in the first embodiment includes countersinks 33-36 associated respectively with the apertures 29-32, whereby the countersinks 33-36 are similar to the countersinks 25 and 26. The first plate 14 in the first embodiment includes slots 37-40 associated respectively with the apertures 29-32, whereby the slots 37-40 are similar to the slots 27 and 28.

The second plate 15 in the first embodiment is substantially, completely identical in design and operation relative to the first plate 14. In that light, and for the sake of brevity, like parts of the second plate 15 have been labeled with like numerals of the first plate 14 on the basis the like parts incorporate a design and function as previously set forth in the description of the first plate 14. Although the second plate 15 in the first embodiment is substantially, completely identical to the first plate 14, one of ordinary skill in the art will recognize alternative shapes, sizes, and orientations for the second plate 15 provided the second plate 15 receives therein an implant 12 also secured with the first plate 14.

As illustrated in FIGS. 3-4D and 5A-6B, a sternal closure system 50 according to a second embodiment includes one or more plate pairs 51 and one or more implants 12. A plate pair 51 in the second embodiment includes a first plate 54 and a second plate 55.

The first plate 54 with reference to FIGS. 4A-4D exhibits a three-dimensional form having a length, width, and height, and, in particular, the first plate 54 includes an upper surface 56 and a lower surface 57 with first and second sides 58 and 59 and first and second ends 60 and 61 therebetween. The upper surface 56 and the lower surface 57 define a height 62 that provides strength to the first plate 54 while a contouring of the upper surface 56 presents the first plate 54 with a lowest possible profile. The lower surface 57 is flat in order for the first plate 54 at its lower surface 57 to seat flush atop a thoracic wall. The first plate 54 in the second embodiment is any suitable biocompatible metal, such as, for example, titanium.

The first plate 54 includes at least a first aperture 63 at the first end 60 extending therethrough from the upper surface 56 to the lower surface 57 and a second aperture 64 adjacent the first aperture 63 extending therethrough from the upper surface 56 to the lower surface 57. The first plate 54 includes the first aperture 63 in order for the first plate 54 to receive therethrough the implant 12. The first plate 54 includes the second aperture 64 in order for the first plate 54 to receive therethrough a fixation device. In the second embodiment, the fixation device is any suitable biocompatible metal screw, such as, for example, titanium, including a non-locking bone screw, a locking bone screw, and a self-tapping bone screw. The first plate 54 at the upper surface 56 and the first aperture 63 is configured to receive therein the implant 12 through a slot 65 extending from the first aperture 63 to the first end 60 of the first plate 54 whereby the slot 65 permits the implant 12 to seat flush in the first plate 54. The first plate 54 at the upper surface 56 and the second aperture 64 is configured to receive therein a screw through a countersink 66 that permits the screw to seat flush in the first plate 54.

While a securing of the first plate 54 to a thoracic wall and a closing of an opening through a sternum requires only the first and second apertures 63 and 64, the first plate 54 in the second embodiment includes an aperture 67 adjacent the second aperture 64 and an aperture 68 adjacent the second end 61 of the first plate 54, whereby the apertures 67 and 68 are similar to the second aperture 64. The first plate 54 in the second embodiment includes countersinks 69 and 70 associated respectively with the apertures 67 and 68, whereby the countersinks 69 and 70 are similar to the countersink 66.

The second plate 55 in the second embodiment is substantially, completely identical in design and operation relative to the first plate 54. In that light, and for the sake of brevity, like parts of the second plate 55 have been labeled with like numerals of the first plate 54 on the basis the like parts incorporate a design and function as previously set forth in the description of the first plate 54. Although the second plate 55 in the second embodiment is substantially, completely identical to the first plate 54, one of ordinary skill in the art will recognize alternative shapes, sizes, and orientations for the second plate 55 provided the second plate 55 receives therein an implant 12 also secured with the first plate 54. Moreover, it should be understood that a first plate 14 or a second plate 15 of the first embodiment may be used in combination with a first plate 54 or a second plate 55 of the second embodiment provided the first plate 14 or the second plate 15 of the first embodiment aligns with the first plate 54 or the second plate 55 of the second embodiment such that an implant 12 secures therebetween.

Figure 5A:
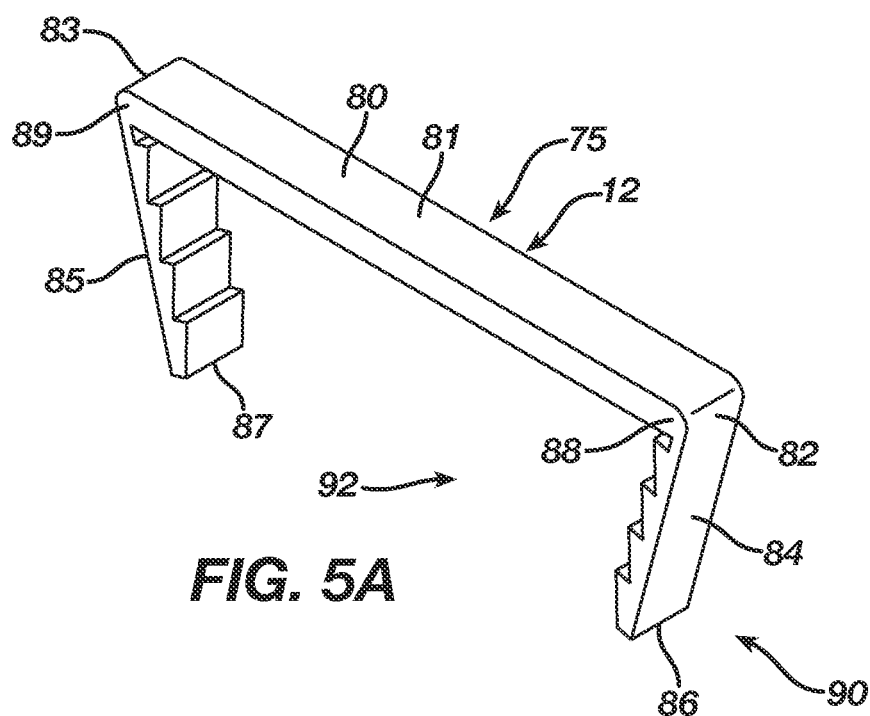
FIG. 5A is an isometric view illustrating an implant for the sternal closure systems according to the first and second embodiments residing in a natural shape.
Figure 5B:
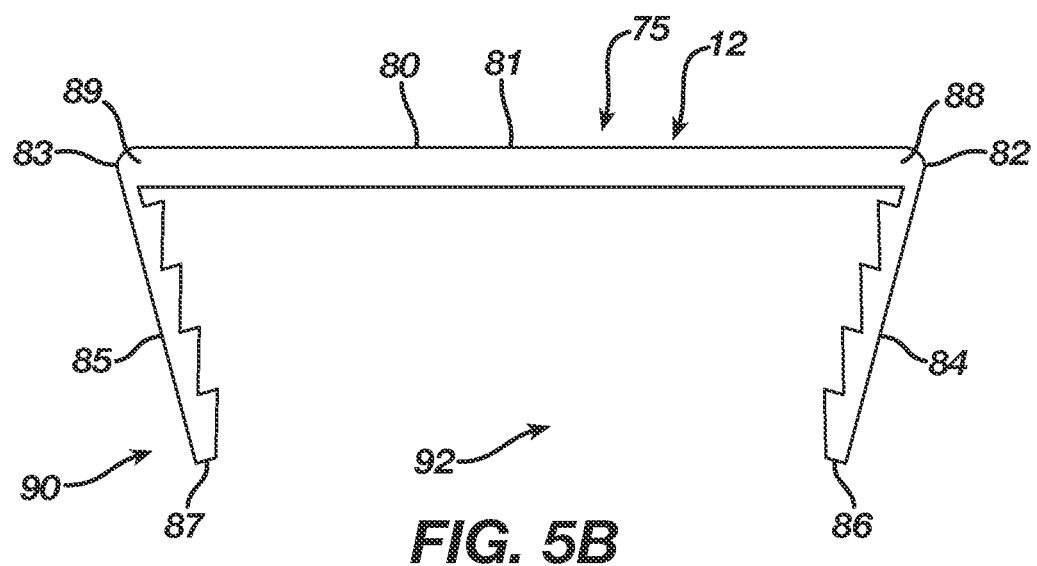
FIG. 5B is a front view illustrating the implant for the sternal closure systems according to the first and second embodiments residing in its natural shape.
Figure 6A:
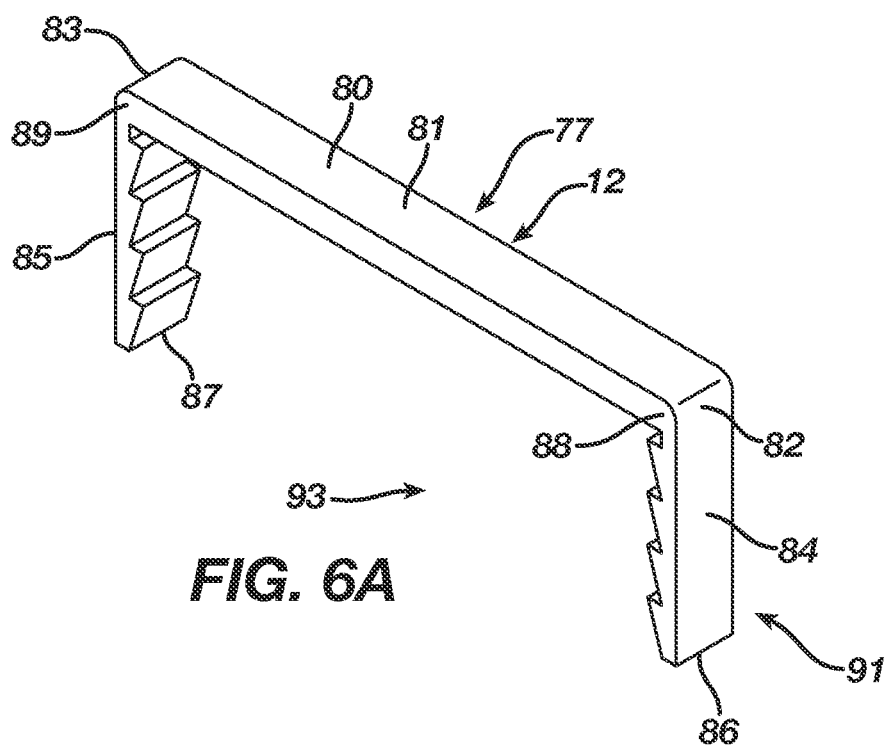
FIG. 6A is an isometric view illustrating the implant for the sternal closure systems according to the first and second embodiments residing in an insertion shape.
Figure 6B:
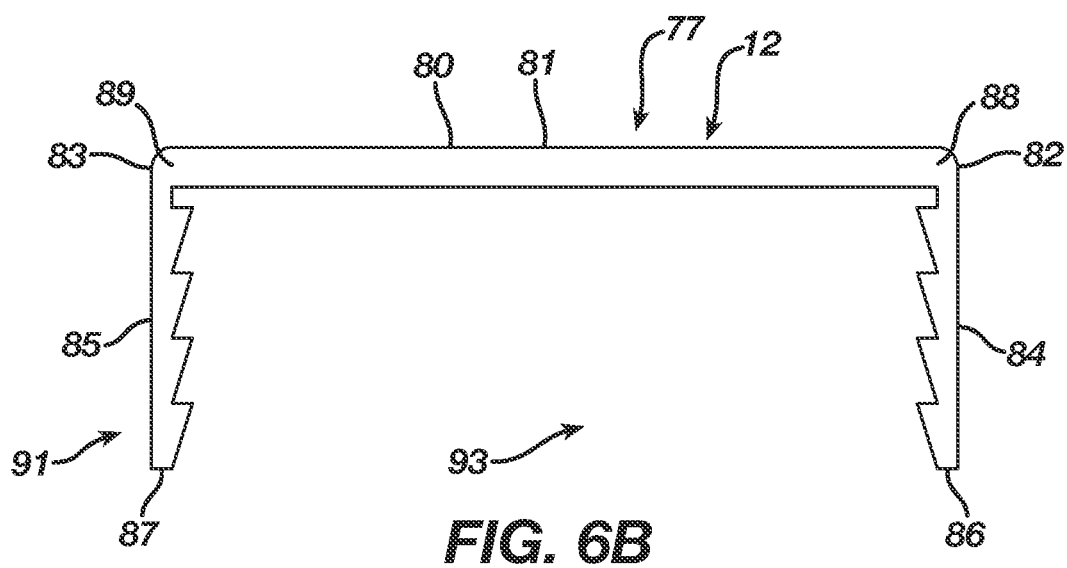
FIG. 6B is a front view illustrating the implant for the sternal closure systems according to the first and second embodiments residing in its insertion shape.

FIGS. 5A-5B illustrate an orthopedic implant 12 in a natural shape 75, whereas FIGS. 6A-6B illustrate the orthopedic implant 5 in an insertion shape 77. Both the sternal closure system 10 according to the first embodiment and the sternal closure system 50 according to the second embodiment include the implant 12. The implant 12 may be manufactured from a shape memory material with superelastic or temperature dependent properties (e.g., Nitinol) such that the implant 12 transitions between its natural shape 75 and its insertion shape 77. The implant 12 when deformed from its natural shape 75 to its insertion shape 77 stores energy deliverable to bone, bones, or bone pieces, and, in particular, to a thoracic wall. In accordance with its manufacture from shape memory material, the implant 12 begins in its natural shape 75, is transitionable to its insertion shape 77, and, once implanted in a thoracic wall, attempts to transition from its insertion shape 77 to its natural shape 75 whereby the implant 12 delivers the energy stored therein to the thoracic wall. More particularly, the implant 12 delivers the energy stored therein to a sternum of the thoracic wall across an opening created in the sternum thereby affixing the opening in the sternum closed and promoting a healing thereof. In the sternal closure systems 10 and 50, attempted transition of the implant 12 from its insertion shape 77 to its natural shape 75 continuously compresses the sternum in order to promote fusion thereof at the opening formed therein.

The implant 12 includes a bridge 80 with a length 81 and having a first end 82, and a second end 83. The implant 12 includes a first leg 84 extending from the bridge 80 at the first end 82 thereof and a second leg 85 extending from the bridge 80 at the second end 83 thereof. The first leg 84, which has a respective tip 86, may include barbs thereon that improve the pull-out resistance of the implant 12. Likewise, the second leg 85, which has a respective tip 87, may include barbs thereon that improve the pull-out resistance of the implant 12. The bridge 80 includes a first transition section 88 located where the first leg 84 extends from the bridge 80, and, in particular, the transition section 88 resides at the first end 82 of the bridge 80. The bridge 80 includes a second transition section 89 located where the second leg 85 extends from the bridge 80, and, in particular, the transition section 89 resides at the second end 83 of the bridge 80.

The natural shape 75 of the implant 12, as illustrated in FIGS. 5A-5B, involves the first and second transition sections 88 and 89, respectively, locating the first leg 84 and the second leg 85 in a natural position 90, which, in the first and second embodiments, is convergent whereby the first leg 84 and the second leg 85 are spaced apart at a first distance 92. Nevertheless, as illustrated in FIGS. 6A-6B, the implant 12 is deformable under the action of superelasticity or temperature dependent shape memory properties to the insertion shape 77 where the first and second transition sections 88 and 89 deform to store energy while also moving, respectively, the first leg 84 and the second leg 85 to an insertion position 91, which, in the first and second embodiments, is substantially parallel whereby the first leg 84 and the second leg 85 are spaced apart at a second distance 93 that is greater than the first distance 92. Since the insertion shape 77 is not the natural shape 75 of the implant 12, the implant 12 at the first and second transition sections 88 and 89 typically is mechanically constrained or the implant 12 is chilled until the implant 12 reaches its martensite phase whereby the first and second transition sections 88 and 89 once deformed maintain the first leg 84 and the second leg 85 in their insertion position 91. A release of a mechanical constraint or a heating of the implant 12 to its austenite phase results in the implant 12 delivering the energy stored in the first and second transition sections 88 and 89 such that the first leg 84 and the second leg 85 attempt to move from their insertion position 91 to their natural position 90 thereby exerting a compressive force after implantation into a sternum across an opening formed therein. Mechanical constraints suitable to engage the implant 12 and maintain the implant 12 in its insertion shape 77 are available from DePuy Synthes Products, Inc., 325 Paramount Drive, Rayham, Mass. 02767, and include forceps, pliers, and implant insertion devices, such as, for example, the implant insertion devices disclosed in U.S. Pat. Nos. 9,585,656 B2 and 10,456,131 B2.

The implant 12 in the first and second embodiments may include multiple variations whereby a length 81 of the bridge 80 and lengths of the first and second legs 84 and 85 of one version are different from the lengths 81 of the bridges 80 and the lengths of the first and second legs 84 and 85 of other versions. The length 81 of the bridge 12 for a version of the implant 12 is determined based upon a bridge size requirement necessary for the implant 12 to span a sternum and achieve a closure of an opening formed in the sternum. Moreover, the lengths of the first and second legs 84 and 85 for a version of the implant 12 is determined based upon a leg seating requirement necessary for the implant 12 to insert into a thoracic wall at an outer cortex thereof and then fixate in the thoracic wall without undue extension of the first and second legs 84 and 85 into the thoracic wall.

Figure 7A:
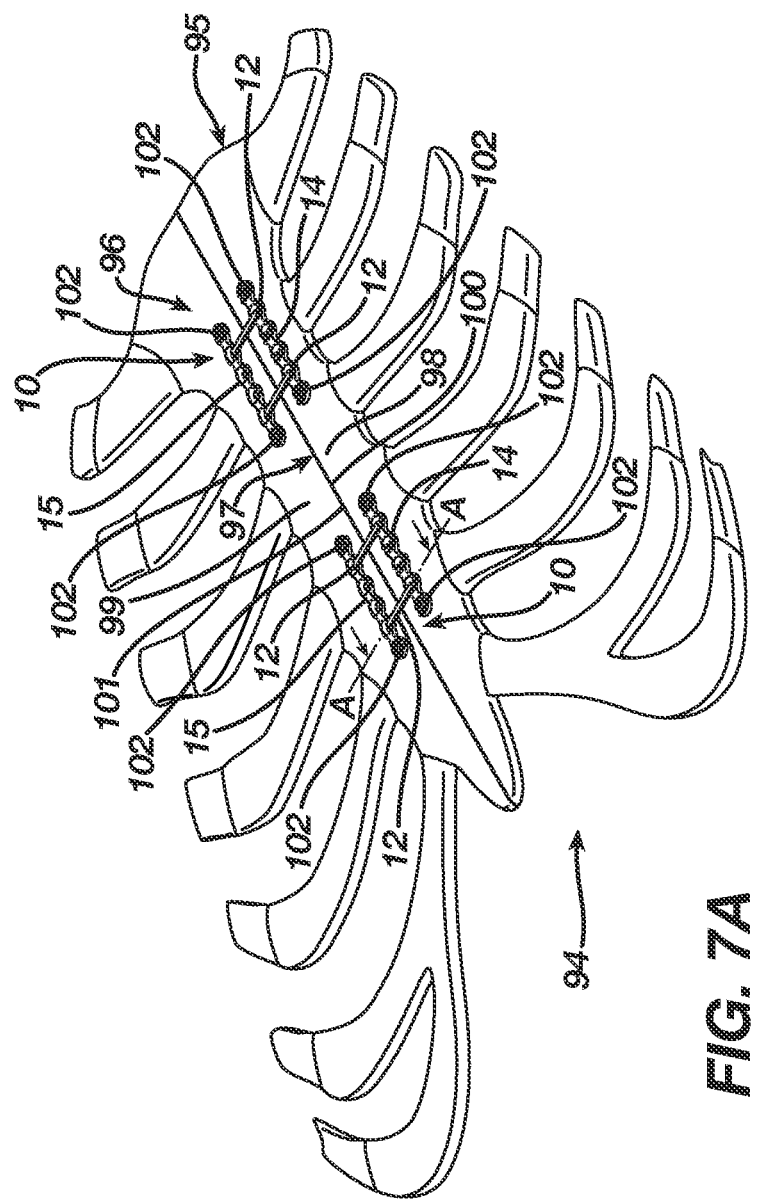
FIG. 7A is an isometric view illustrating the sternal closure system according to the first embodiment as utilized in closing a sternum.
Figure 7B:
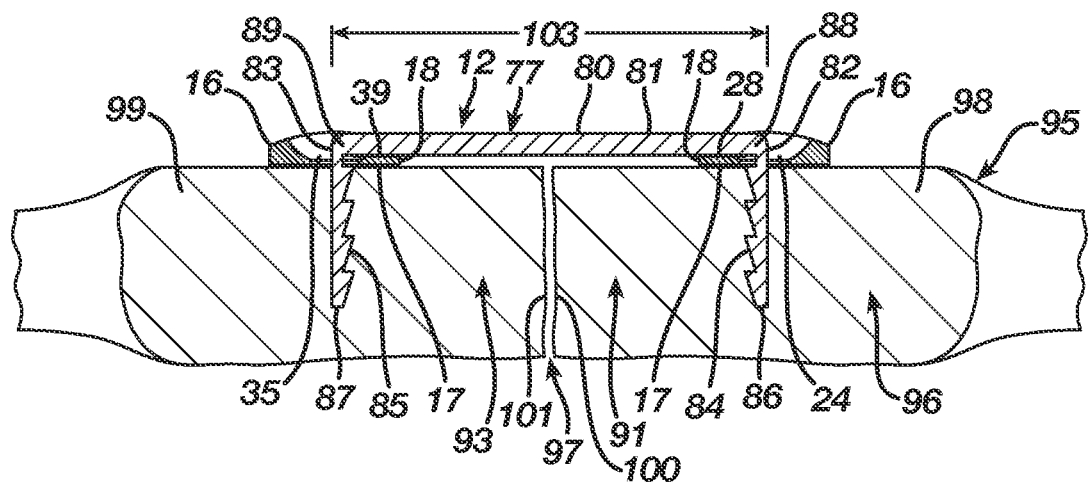
FIG. 7B is a cross-sectional view taken along lines A-A of FIG. 7A illustrating the sternal closure system according to the first embodiment as utilized in closing a sternum whereby the implant resides in its insertion shape.
Figure 7C:
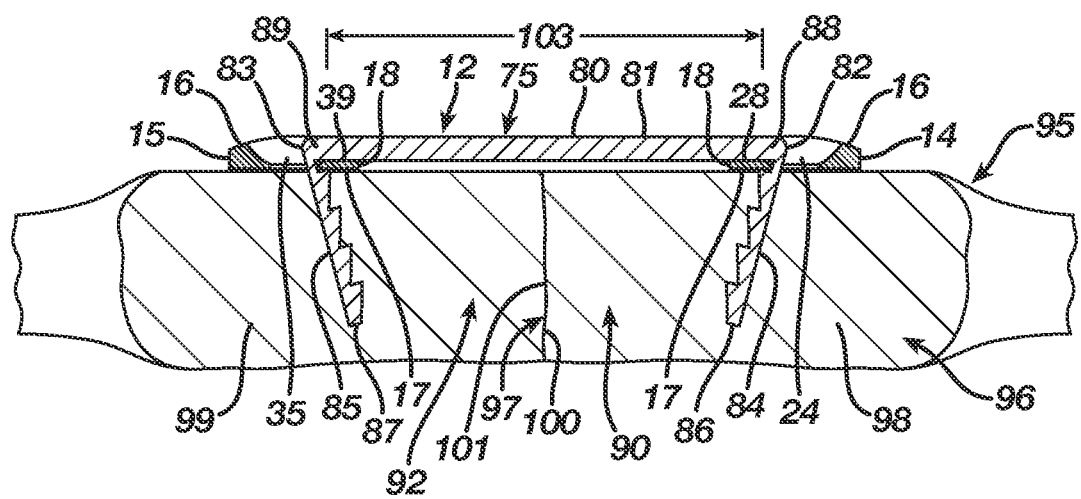
FIG. 7C is a cross-sectional view taken along lines A-A of FIG. 7A illustrating the sternal closure system according to the first embodiment as utilized in closing a sternum whereby the implant attempts transition to its natural shape.

FIGS. 7A-7C illustrate the sternal closure system 10 according to the first embodiment as utilized during a surgery involving access into a thoracic cavity 94 through a thoracic wall 95. To access the thoracic cavity 94, a sternum 96 of the thoracic wall 95 is perforated thereby forming therein an opening 97 through which the thoracic cavity 94 is accessed. The perforation of the sternum 96 through the forming of the opening 97 therein creates a first segment 98 and a second segment 99 in the sternum 96, while the opening 97 includes a first side 100 and a second side 101. Upon completion of the surgery, the thoracic wall 95, and, in particular, the sternum 96 at its first and second segments 98 and 99, is manipulated such that the opening 97 closes along its first and second sides 100 and 101 and then is held closed using a suitable device or devices, such as, for example, a clamp or clamps.

With the opening 97 in the sternum 96 held closed, one or more sternal closure systems 10 according to the first embodiment are secured with the thoracic wall 95 in order to maintain the opening 97 in the sternum 96 closed. More particularly, a first plate 14 at its lower surface 17 is placed atop the sternum 96 at the first segment 98 thereof adjacent the first side 100 of the opening 97. The first plate 14 resides substantially parallel with the opening 97 in an orientation whereby the first side 18 of the first plate 14 and thus the slots 27-28 and 37-40 face the opening 97. Likewise, a second plate 15 at its lower surface 17 is placed atop the sternum 96 at the second segment 99 thereof adjacent the second side 101 of the opening 97. The second plate 15 resides substantially parallel with the opening 97 in an orientation whereby the first side 18 of the second plate 15 and thus the slots 27-28 and 37-40 face the opening 97. The first plate 14 and the second plate 15 align across the opening 97 and are spaced apart such that one or more implants 12 implanted in the sternum 96 across the opening 97 secure with the first plate 14 and with the second plate 15.

Illustratively, referring specifically to FIGS. 7B and 7C, the aperture 24 of the first plate 14 aligns across the opening 97 with the aperture 35 of the second plate 15 and is separated a distance 103 substantially equal to the length 81 of the bridge 80 for the implant 12 and the second distance 93 between the first leg 84 and the second leg 85 of the implant 12 when the first and second legs 84 and 85 reside in their insertion position 91. Similarly, the apertures 23, 29, 30, 31, and 32 of the first plate 14 align respectively with the apertures 32, 30, 29, 24, and 23 of the second plate 15 and are spaced apart across the opening 97 by the distance 103. Moreover, the slot 28 at the aperture 24 of the first plate 14 aligns across the opening 97 with the slot 39 at the aperture 35 of the second plate 15. Similarly, the slots 27, 37, 38, 39, and 40 at the apertures 23, 29, 30, 31, and 32 of the first plate 14 align across the opening 97 with the slots 40, 38, 37, 28, and 27 at the apertures 32, 30, 29, 24, and 23 of the second plate 15.

After placement of the first plate 14 atop the first segment 98 of the sternum 96 and the second plate 15 atop the second segment 99 of the sternum 96, including the alignment and spacing apart thereof as previously described, the first plate 14 and the second plate 15 secure with the sternum 96 via fixation devices, such as, for example, screws 102. Illustratively, referring specifically to FIG. 7A, screws 102, which may be self-tapping bone screws, insert into the first plate 14 through the apertures 23 and 32 of the first plate 14 and engage the first segment 98 of the sternum 96. The screws 102 enter the first segment 98 of the sternum 96 until the screws 102 seat within the countersinks 25 and 36 of the first plate 14 and thus reside flush with the upper surface 16 of the first plate 14. Likewise, screws 102 insert into the second plate 15 through the apertures 32 and 23 of the second plate 15 and enter the second segment 99 of the sternum 96 until the screws 102 seat within the countersinks 36 and 25 of the second plate 15 and thus reside flush with the upper surface 16 of the second plate 15. The screws 102 engage the sternum 96 at an outer cortex thereof in order to fixate the first plate 14 atop the first segment 98 of the sternum 96 and the second plate 15 atop the second segment 99 of the sternum 96 whereby the first plate 14 and the second plate 15 at their apertures 23-24 and 29-32 are separated across the opening 97 by the distance 103.

Alternatively, holes created to assist in the insertion of the screws 102, which may be non-locking or locking bone screws, may be drilled into the first segment 98 of the sternum 96 at the apertures 23 and 32 of the first plate 14. The screws 102 insert into the first plate 14 through the apertures 23 and 32 of the first plate 14 and then into the first segment 98 of the sternum 96 via the holes such that the screws 102 engage the first segment 98 of the sternum 96. The screws 102 enter the first segment 98 of the sternum 96 until the screws 102 seat within the countersinks 25 and 36 of the first plate 14 and thus reside flush with the upper surface 16 of the first plate 14. Likewise, holes created to assist in the insertion of the screws 102 may be drilled into the second segment 99 of the sternum 96 at the apertures 32 and 23 of the second plate 15. The screws 102 insert into the second plate 15 through the apertures 32 and 23 of the second plate 15 and then into the second segment 99 of the sternum 96 via the holes such that the screws 102 engage the second segment 99 of the sternum 96. The screws 102 enter the second segment 99 of the sternum 96 until the screws 102 seat within the countersinks 36 and 25 of the second plate 15 and thus reside flush with the upper surface 16 of the second plate 15. The screws 102 engage the sternum 96 at an outer cortex thereof in order to fixate the first plate 14 atop the first segment 98 of the sternum 96 and the second plate 15 atop the second segment 99 of the sternum 96 whereby the first plate 14 and the second plate 15 at their apertures 23-24 and 29-32 are separated across the opening 97 by the distance 103. It should be understood that additional screws 102 may be inserted through additional apertures 24 and 29-31 of the first and second plates 14 and 15 and into the sternum 96 at an outer cortex thereof in order to fixate the first and second plates 14 and 15 atop the sternum 96.

Upon fixation of the first plate 14 atop the first segment 98 of the sternum 96 and the second plate 15 atop the second segment 99 of the sternum 96 with the apertures 23-24 and 29-32 thereof separated across the opening 97 by the distance 103, one or more implants 12 that interconnect the first plate 14 and the second plate 15 hold the opening 97 in the sternum 96 closed along its first and second sides 100 and 101 and promote a healing of the sternum 96 at the opening 97 therein. Illustratively, referring specifically to FIGS. 7B and 7C, an implant 12, while held, for example, by an implant insertion device, in its insertion shape 77 whereby the first leg 84 and the second leg 85 in their insertion position 91 are spaced apart the second distance 93, is introduced into the first plate 14 and the second plate 15 at their respective apertures 24 and 35. The implant 12, and, more particularly, the first and second legs 84 and 85, respectively, due to the distance 103 between the apertures 24 and 35 of the first and second plates 14 and 15 being substantially equal to the length 81 of the bridge 80 and the second distance 93 of the first and second legs 84 and 85 in their insertion position 91, insert into the apertures 24 and 35. The first leg 84 passes through the aperture 24 and inserts into the first segment 98 of the sternum 96 until the bridge 80 at the first end 82 thereof seats in the slot 28 and thus resides flush with the upper surface 16 of the first plate 14. Likewise, the second leg 85 passes through the aperture 35 and inserts into the second segment 99 of the sternum 96 until the bridge 80 at the second end 83 thereof seats in the slot 39 and thus resides flush with the upper surface 16 of the second plate 15. If desired or necessary, a respective hole created to assist in the insertion of the first and second legs 84 and 85 may be drilled into the first segment 98 of the sternum 96 at the aperture 24 and the second segment 99 of the sternum 96 at the aperture 35.

With the first leg 84 inserted through the aperture 24 and into the first segment 98 of the sternum 96 and the second leg 85 inserted through the aperture 35 and into the second segment 99 of the sternum 96, the implant 12 is released, which, by way of example, involves disengaging the implant insertion device from the implant 12. After release of the implant 12, the implant 12 at its bridge 80, if necessary, may be tamped until the bridge 80 at its first and second ends 82 and 83, respectively, seats within the slots 28 and 39 and thus resides flush with the upper surfaces 16 of the first and second plates 14 and 15. The released implant 12, due to its superelasticity or a heating thereof, delivers the energy stored in its first and second transition sections 88 and 89, resulting in the implant 12 attempting to transition from its insertion shape 77 to its natural shape 75 whereby the first leg 84 and the second leg 85 attempt to move from their insertion position 91 at the second distance 93 to their natural position 90 at the first distance 92. The implant 12, consequently, exerts a compressive force to the sternum 96 at the first and second segments 98 and 99 across the opening 97 therein. The first leg 84 and the second leg 85, accordingly, engage the sternum 96 at an outer cortex thereof in order to fixate the implant 12 with its bridge 80 traversing the sternum 96 at the opening 97 such that the implant 12 holds the opening 97 closed at its first and second sides 100 and 101.

While the implant 12 exerts the compressive force to the sternum 96 across the opening 97 thereby holding the opening 97 closed, the implant 12 further engages with the first plate 14 and with the second plate 15 in order for the first and second plates 14 and 15 to assist in maintaining the implant 12 fastened with the sternum 96 whereby the implant 12 is not subject to a movement about the sternum 96, a loosening relative to the sternum 96, or a dislodgement from the sternum 96 that causes a re-opening of the sternum 96 at the opening 97. More particularly, the first leg 84 adjacent the transition section 88 pivots underneath the first plate 14 at its lower surface 17 in a movement toward the first side 18 of the first plate 14 whereby the first leg 84 engages the lower surface 17 of the first plate 14 at a location below the slot 28 of the first plate 14. The first plate 14, accordingly, through its engagement with the sternum 96 via the screws 102 and further with the first leg 84 of the implant 12, assists in affixing the implant 12 with the sternum 96 such that the implant 12 remains secured with the sternum 96 and is not subject to movement, loosening, or dislodgement. Likewise, the second leg 85 adjacent the transition section 89 pivots underneath the second plate 15 at its lower surface 17 in a movement toward the first side 18 of the second plate 15 whereby the second leg 85 engages the lower surface 17 of the second plate 15 at a location below the slot 28 of the second plate 15. The second plate 15, accordingly, through its engagement with the sternum 96 via the screws 102 and further with the second leg 85 of the implant 12, assists in affixing the implant 12 with the sternum 96 such that the implant 12 remains secured with the sternum 96 and is not subject to movement, loosening, or dislodgement. It should be understood that, although the first plate 14 has been described as substantially, completely aligning with the second plate 15, the first plate 14 may be offset from the second plate 15 as long as at least one of the apertures 23-24 and 29-32 of the first plate 14 aligns with at least one of the apertures 23-24 and 29-32 of the second plate 15 in order to receive an implant 12 therethrough.

Even though a single sternal closure system 10 according to the first embodiment with a single implant 12 will hold closed the opening 97 in the sternum 96, an additional implant 12 or implants 12 may be implanted in the sternum 96 across the opening 97 while also engaging with the first and second plates 14 and 15. The additional implants 12 implant in the sternum 96 across the opening 97 and engage with the first and second plates 14 and 15 as previously described with reference to the single implant 12. Moreover, an additional sternal closure system 10 or sternal closure systems 10 may be secured with the sternum 96 across the opening 97. The additional sternal closure systems 10 secure with the sternum 96 across the opening 97 as previously described with reference to the single sternal closure system 10. Once the one or more sternal closure systems 10 secure with the sternum 96 across the opening 97, any clamps holding the sternum 96 closed are removed in order to permit completion of the surgery. The one or more sternal closure systems 10 secured with the sternum 96 across the opening 97 may remain after the surgery or alternatively may be removed at a later date after a healing of the sternum 96.

Although the one or more implants 12 compress the sternum 96 at the opening 97 while remaining securely fastened therewith due to their engagement with the first and second plates 14 and 15, each implant 12 in an emergency situation requiring an intervention through the sternum 96 may be quickly removed by a pulling of the implant 12 from the sternum 96 and the first and second plates 14 and 15. The implant 12 at its first and second legs 84 and 85, due to its construction from a flexible and thus deformable shape memory material, releases from the sternum 96 and the first and second plates 14 and 15 such that the thoracic cavity 94 may be accessed through the sternum 96 via a re-opened opening 97.

Figure 8A:
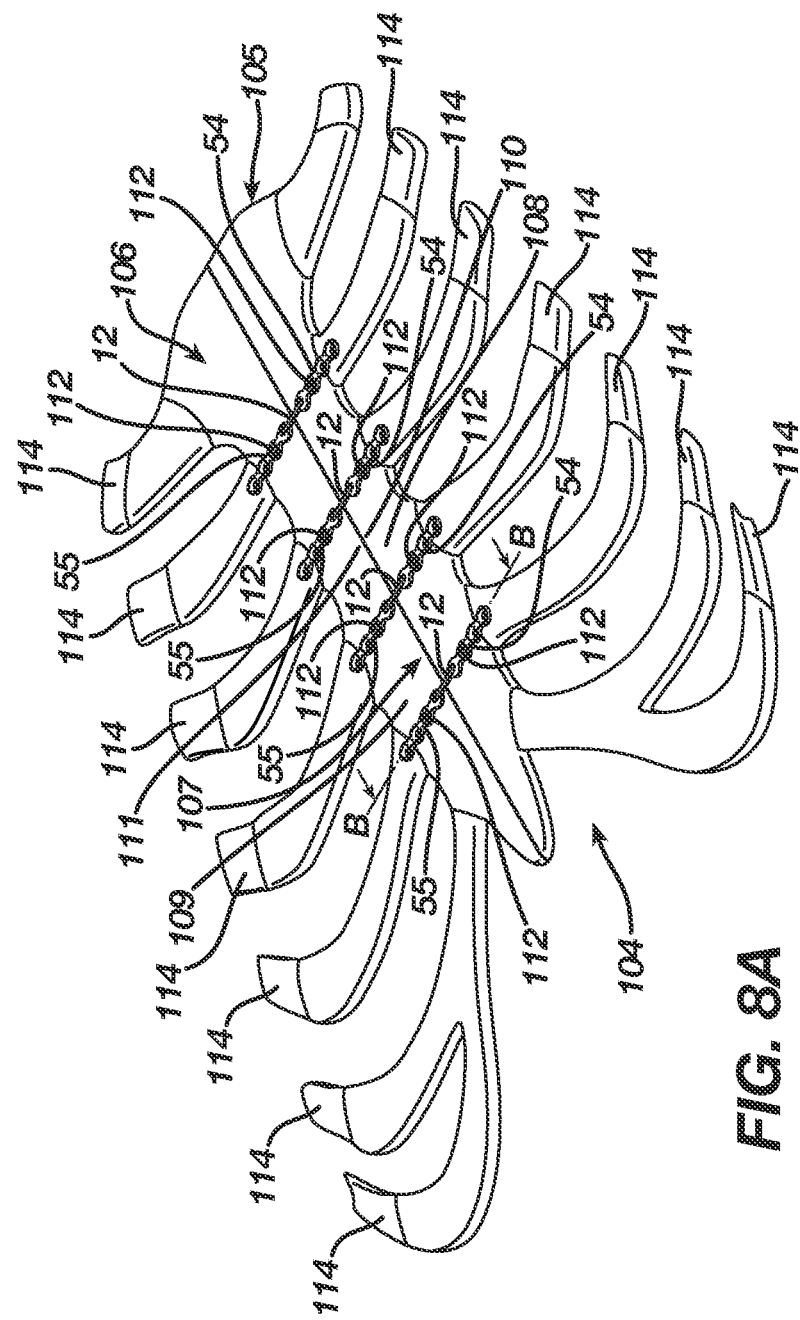
FIG. 8A is an isometric view illustrating the sternal closure system according to the second embodiment as utilized in closing a sternum.

FIGS. 8A-8C illustrate the sternal closure system 50 according to the second embodiment as utilized during a surgery involving access into a thoracic cavity 104 through a thoracic wall 105. To access the thoracic cavity 104, a sternum 106 of the thoracic wall 105 is perforated thereby forming therein an opening 107 through which the thoracic cavity 104 is accessed. The perforation of the sternum 106 through the forming of the opening 107 therein creates a first segment 108 and a second segment 109 in the sternum 106, while the opening 107 includes a first side 110 and a second side 111. Upon completion of the surgery, the thoracic wall 105, and, in particular, the sternum 106 at its first and second segments 108 and 109, is manipulated such that the opening 107 closes along its first and second sides 110 and 111 and then is held closed using a suitable device or devices, such as, for example, a clamp or clamps.

With the opening 107 in the sternum 106 held closed, one or more sternal closure systems 50 according to the second embodiment are secured with the thoracic wall 105 in order to maintain the opening 107 in the sternum 106 closed. More particularly, a first plate 54 at its lower surface 57 is placed atop the sternum 106 at the first segment 108 thereof adjacent the first side 110 of the opening 107. The first plate 54 resides substantially perpendicular with the opening 107 in an orientation whereby the first end 60 of the first plate 54 and thus the slot 65 face the opening 107. The first plate 54 resides atop the sternum 106, or, alternatively, depending upon the size of the first plate 54 and/or the sternum 106, the first plate 54 may extend from atop the sternum 106 to a location atop one of the ribs 114 for the thoracic cavity 105. Likewise, a second plate 55 at its lower surface 57 is placed atop the sternum 106 at the second segment 109 thereof adjacent the second side 111 of the opening 107. The second plate 55 resides substantially perpendicular with the opening 107 in an orientation whereby the first end 60 of the second plate 55 and thus the slot 65 face the opening 107. The second plate 55 resides atop the sternum 106, or, alternatively, depending upon the size of the second plate 55 and/or the sternum 106, the second plate 55 may extend from atop the sternum 106 to a location atop one of the ribs 114 for the thoracic cavity 105. The first plate 54 and the second plate 55 align across the opening 107 and are spaced apart such that an implant 12 implanted in the sternum 106 across the opening 107 secures with the first plate 54 and with the second plate 55. Illustratively, referring specifically to FIGS. 8B and 8C, the aperture 63 of the first plate 54 aligns across the opening 107 with the aperture 63 of the second plate 55 and is separated a distance 113 substantially equal to the length 81 of the bridge 80 for the implant 12 and the second distance 93 between the first leg 84 and the second leg 85 of the implant 12 when the first and second legs 84 and 85 reside in their insertion position 91. Moreover, the slot 65 at the aperture 63 of the first plate 54 aligns across the opening 107 with the slot 65 at the aperture 63 of the second plate 55.

After placement of the first plate 54 atop the first segment 108 of the sternum 106 and the second plate 55 atop the second segment 109 of the sternum 106, including the alignment and spacing apart thereof as previously described, the first plate 54 and the second plate 55 secure with the sternum 106 via fixation devices, such as, for example, screws 112. Illustratively, a screw 112, which may be self-tapping bone screws, inserts into the first plate 54 through the aperture 64 of the first plate 54 and engages the first segment 108 of the sternum 106. The screw 112 enters the first segment 108 of the sternum 106 until the screw 112 seats within the countersink 66 of the first plate 54 and thus resides flush with the upper surface 56 of the first plate 54. Likewise, a screw 112 inserts into the second plate 55 through the aperture 64 of the second plate 55 and enters the second segment 109 of the sternum 106 until the screw 112 seats within the countersinks 66 of the second plate 55 and thus resides flush with the upper surface 56 of the second plate 55. The screws 112 engage the sternum 106 at an outer cortex thereof in order to fixate the first plate 54 atop the first segment 108 of the sternum 106 and the second plate 55 atop the second segment 109 of the sternum 106 whereby the first plate 54 and the second plate 55 at their apertures 63 are separated across the opening 107 by the distance 113.

Alternatively, a hole created to assist in the insertion of the screw 112, which may be a non-locking or locking bone screw, may be drilled into the first segment 108 of the sternum 106 at the aperture 64 of the first plate 54. The screw 112 inserts into the first plate 54 through the aperture 64 of the first plate 54 and then into the first segment 108 of the sternum 106 via the hole such that the screw 112 engages the first segment 108 of the sternum 106. The screw 112 enters the first segment 108 of the sternum 106 until the screw 112 seats within the countersink 66 of the first plate 54 and thus resides flush with the upper surface 56 of the first plate 54. Likewise, a hole created to assist in the insertion of the screw 112, which may be a non-locking or locking bone screw, may be drilled into the second segment 109 of the sternum 106 at the aperture 64 of the second plate 55. The screw 112 inserts into the second plate 55 through the aperture 64 of the second plate 55 and then into the second segment 109 of the sternum 106 via the hole such that the screw 112 engages the second segment 109 of the sternum 106. The screw 112 enters the second segment 109 of the sternum 106 until the screw 112 seats within the countersink 66 of the second plate 55 and thus resides flush with the upper surface 56 of the second plate 55. The screws 112 engage the sternum 106 at an outer cortex thereof in order to fixate the first plate 54 atop the first segment 108 of the sternum 106 and the second plate 55 atop the second segment 109 of the sternum 106 whereby the first plate 54 and the second plate 55 at their apertures 63 are separated across the opening 107 by the distance 113. It should be understood that additional screws 112 may be inserted through additional apertures 67 and 68 of the first and second plates 54 and 55 and into the sternum 106 at an outer cortex thereof in order to fixate the first and second plates 54 and 55 atop the sternum 106. If the first and second plates 54 and 55 at their apertures 68 extend to a location atop one of the ribs 114 for the thoracic cavity 105, additional screws 112 may be inserted through the apertures 68 of the first and second plates 54 and 55 and into the ribs 114 at an outer cortex thereof in order to assist in fixating the first and second plates 54 and 55 atop the sternum 106.

Upon fixation of the first plate 54 atop the first segment 108 of the sternum 106 and the second plate 55 atop the second segment 109 of the sternum 106 with the apertures 63 thereof separated across the opening 107 by the distance 113, an implant 12 that interconnects the first plate 54 and the second plate 55 holds the opening 107 in the sternum 106 closed along its first and second sides 110 and 111 and promotes a healing of the sternum 106 at the opening 107 therein. Illustratively, referring specifically to FIGS. 8B and 8C, the implant 12, while held, for example, by an implant insertion device, in its insertion shape 77 whereby the first leg 84 and the second leg 85 in their insertion position 91 are spaced apart the second distance 93, is introduced into the first plate 54 and the second plate 55 at their respective apertures 63. The implant 12, and, more particularly, the first and second legs 84 and 85, respectively, due to the distance 113 between the apertures 63 of the first and second plates 54 and 55 being substantially equal to the length 81 of the bridge 80 and the second distance 93 of the first and second legs 84 and 85 in their insertion position 91, insert into the apertures 63 of the first and second plates 54 and 55. The first leg 84 passes through the aperture 63 of the first plate 54 and inserts into the first segment 108 of the sternum 106 until the bridge 80 at the first end 82 thereof seats in the slot 65 of the first plate 54 and thus resides flush with the upper surface 56 of the first plate 54. Likewise, the second leg 85 passes through the aperture 63 of the second plate 55 and inserts into the second segment 109 of the sternum 106 until the bridge 80 at the second end 83 thereof seats in the slot 65 of the second plate 55 and thus resides flush with the upper surface 56 of the second plate 55. If desired or necessary, a respective hole created to assist in the insertion of the first and second legs 84 and 85 may be drilled into the first segment 108 of the sternum 106 at the aperture 63 of the first plate 54 and the second segment 109 of the sternum 106 at the aperture 63 of the second plate 55.

With the first leg 84 inserted through the aperture 63 of the first plate 54 and into the first segment 108 of the sternum 106 and the second leg 85 inserted through the aperture 63 of the second plate 55 and into the second segment 109 of the sternum 106, the implant 12 is released, which, by way of example, involves disengaging the implant insertion device from the implant 12. After release of the implant 12, the implant 12 at its bridge 80, if necessary, may be tamped until the bridge 80 at its first and second ends 82 and 83, respectively, seats within the slots 65 of the first and second plates 54 and 55 and thus resides flush with the upper surfaces 56 of the first and second plates 54 and 55. The released implant 12, due to its superelasticity or a heating thereof, delivers the energy stored in its first and second transition sections 88 and 89, resulting in the implant 12 attempting to transition from its insertion shape 77 to its natural shape 75 whereby the first leg 84 and the second leg 85 attempt to move from their insertion position 91 at the second distance 93 to their natural position 90 at the first distance 92. The implant 12, consequently, exerts a compressive force to the sternum 106 at the first and second segments 108 and 109 across the opening 107 therein. The first leg 84 and the second leg 85, accordingly, engage the sternum 106 at an outer cortex thereof in order to fixate the implant 12 with its bridge 80 traversing the sternum 106 at the opening 107 such that the implant 12 holds the opening 107 closed at its first and second sides 110 and 111.

While the implant 12 exerts the compressive force to the sternum 106 across the opening 107 thereby holding the opening 107 closed, the implant 12 further engages with the first plate 54 and with the second plate 55 in order for the first and second plates 54 and 55 to assist in maintaining the implant 12 fastened with the sternum 106 whereby the implant 12 is not subject to a movement about the sternum 106, a loosening relative to the sternum 106, or a dislodgement from the sternum 106 that causes a re-opening of the sternum 106 at the opening 107. More particularly, the first leg 84 adjacent the transition section 88 pivots underneath the first plate 54 at its lower surface 57 in a movement toward the first end 60 of the first plate 54 whereby the first leg 84 engages the lower surface 57 of the first plate 54 at a location below the slot 65 of the first plate 54. The first plate 54, accordingly, through its engagement with the sternum 106 via the screw 112 and further with the first leg 84 of the implant 12, assists in affixing the implant 12 with the sternum 106 such that the implant 12 remains secured with the sternum 106 and is not subject to movement, loosening, or dislodgement. Likewise, the second leg 85 adjacent the transition section 89 pivots underneath the second plate 55 at its lower surface 57 in a movement toward the first end 60 of the second plate 55 whereby the second leg 85 engages the lower surface 57 of the second plate 55 at a location below the slot 65 of the second plate 55. The second plate 55, accordingly, through its engagement with the sternum 106 via the screw 112 and further with the second leg 85 of the implant 12, assists in affixing the implant 12 with the sternum 106 such that the implant 12 remains secured with the sternum 106 and is not subject to movement, loosening, or dislodgement.

Even though a single sternal closure system 50 according to the second embodiment will hold closed the opening 107 in the sternum 106, an additional sternal closure system 50 or sternal closure systems 50 may be secured with the sternum 106 across the opening 107. The additional sternal closure systems 50 secure with the sternum 106 across the opening 107 as previously described with reference to the single sternal closure system 50. Once the one or more sternal closure systems 50 secure with the sternum 106 across the opening 107, any clamps holding the sternum 106 closed are removed in order to permit completion of the surgery. The one or more sternal closure systems 50 secured with the sternum 106 across the opening 107 may remain after the surgery or alternatively may be removed at a later date after a healing of the sternum 106.

Although the one or more implants 12 compress the sternum 106 at the opening 107 while remaining securely fastened therewith due to their engagement with the first and second plates 54 and 55, each implant 12 in an emergency situation requiring an intervention through the sternum 106 may be quickly removed by a pulling of the implant 12 from the sternum 106 and the first and second plates 54 and 55. The implant 12 at its first and second legs 84 and 85, due to its construction from a flexible and thus deformable shape memory material, releases from the sternum 106 and the first and second plates 54 and 55 such that the thoracic cavity 104 may be accessed through the sternum 106 via a re-opened opening 107.

A feature of the sternal closure system 10 according to the first embodiment and the sternal closure system 50 according to the second embodiment includes their interchangeability. A first plate 14 or a second plate 15 of the sternal closure system 10 may be utilized with a first plate 54 or a second plate 55 of the sternal closure system 50. As an illustration, a first plate 54 is placed atop a sternum adjacent a first side of an opening therein with the first plate 54 residing substantially perpendicular with the opening in an orientation whereby the first end 60 of the first plate 54 and thus the slot 65 face the opening. Similarly, a second plate 15 is placed atop the sternum adjacent a second side of the opening 97 with second plate 15 residing substantially parallel with the opening in an orientation whereby the first side 18 of the second plate 15 and thus the slots 27-28 and 37-40 face the opening. The aperture 63 of the first plate 54 aligns across the opening and is spaced apart from one of the apertures 23-24 and 29-32 of the second plate 15 a distance substantially equal to the length 81 of the bridge 80 for the implant 12 and the second distance 93 between the first leg 84 and the second leg 85 of the implant 12 when the first and second legs 84 and 85 reside in their insertion position 91. Moreover, the slot 65 of the first plate 54 aligns across the opening with one of the slots 27-28 and 37-40. After placement of the first plate 54 and the second plate 15 atop the sternum, including the above-described alignment and spacing apart thereof, the first plate 54 and the second plate 15 secure with the sternum via fixation devices as previously described. Upon fixation of the first plate 54 and the second plate 15 atop the sternum, an implant 12 inserts through the first plate 54 and the second plate 15 and into the sternum as previously described in order to hold the opening in the sternum closed and promote a healing thereof. Once the implant 12, the first plate 54, and the second plate 15 secure with the sternum across the opening, any clamps holding the sternum closed are removed followed by a completion of the surgery.

Figure 9A:
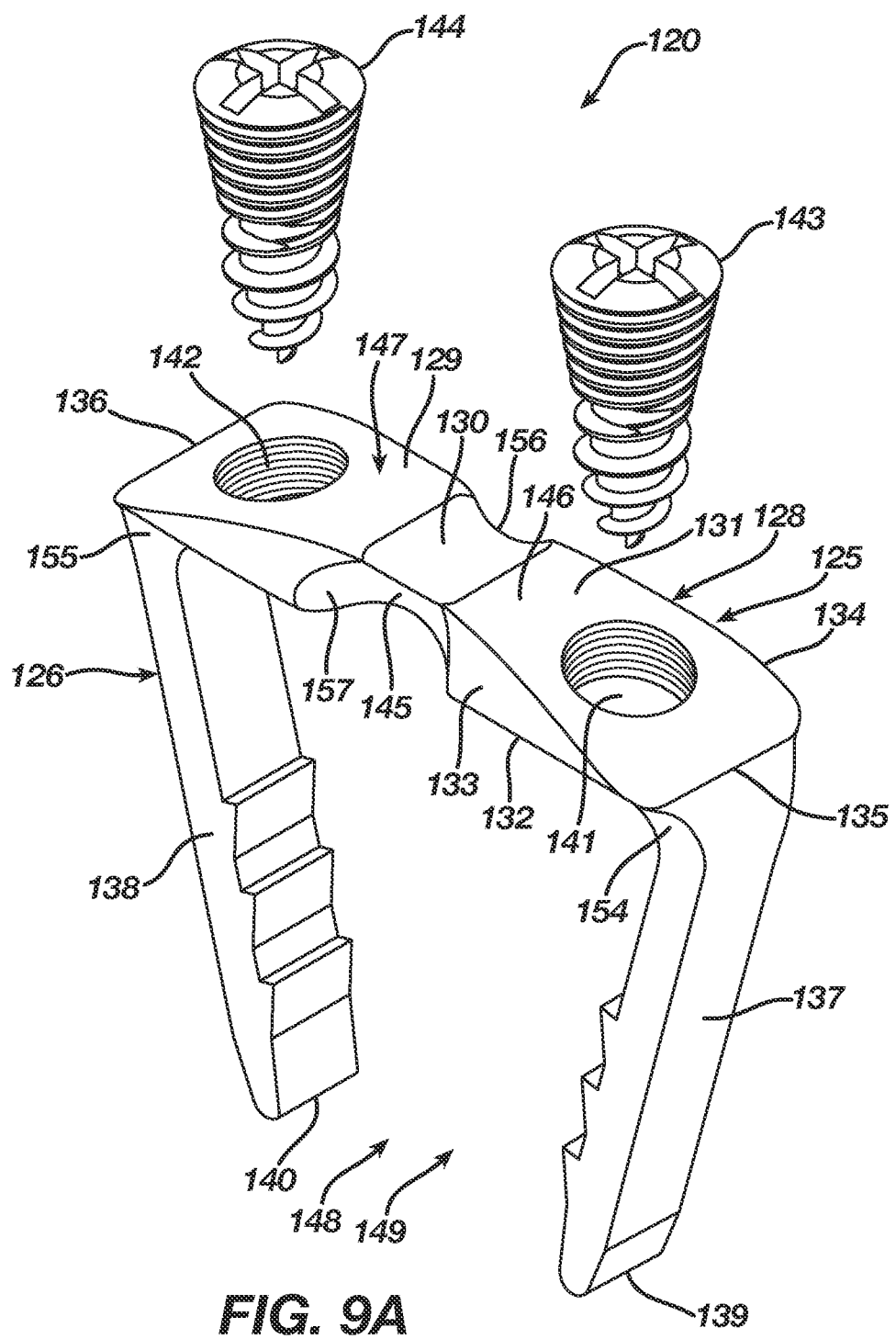
FIG. 9A is an isometric view illustrating a sternal closure system according to a third embodiment whereby an implant thereof resides in a natural shape and screws thereof reside exterior of the implant.
Figure 9B:
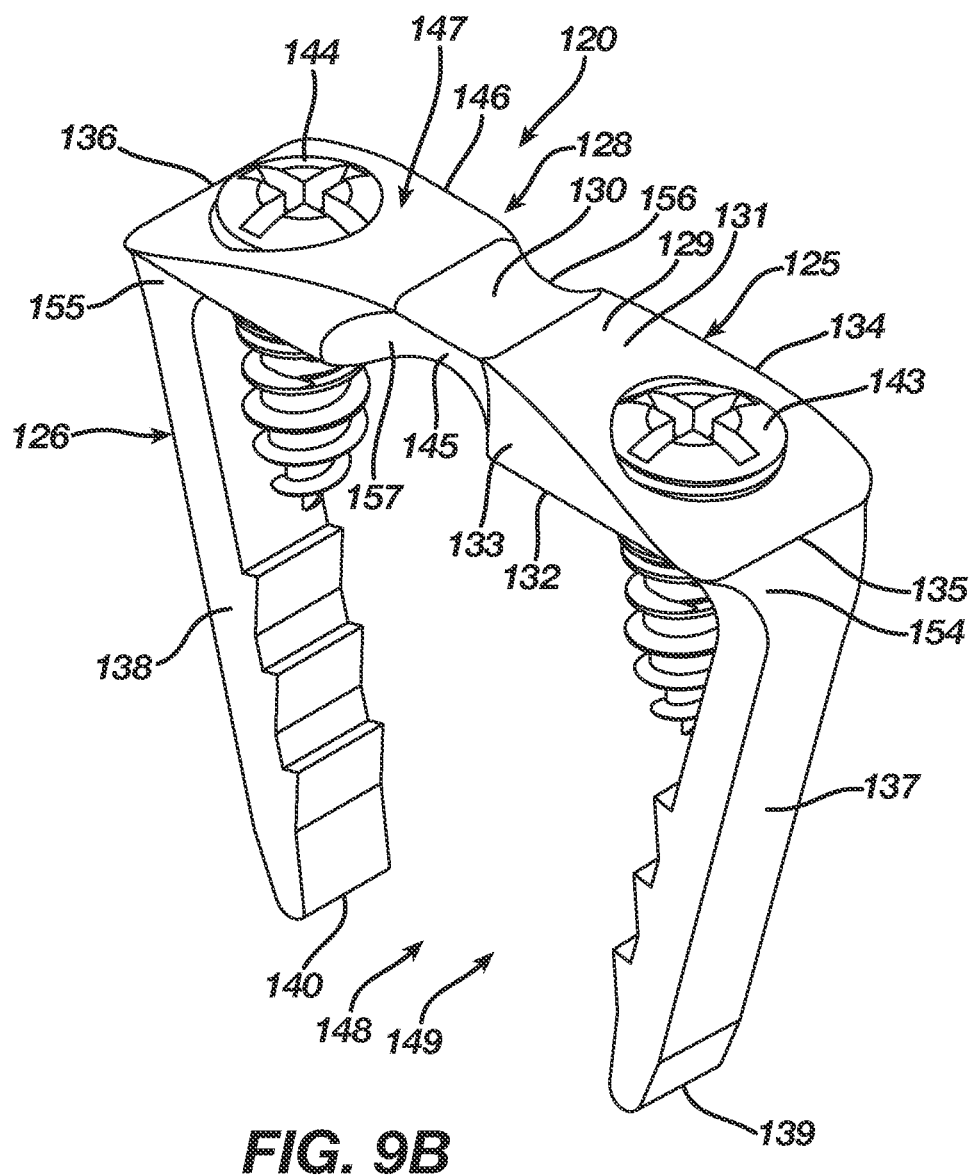
FIG. 9B is an isometric view illustrating the sternal closure system according to the third embodiment whereby the implant thereof resides in its natural shape and screws thereof engage the implant.
Figure 9C:
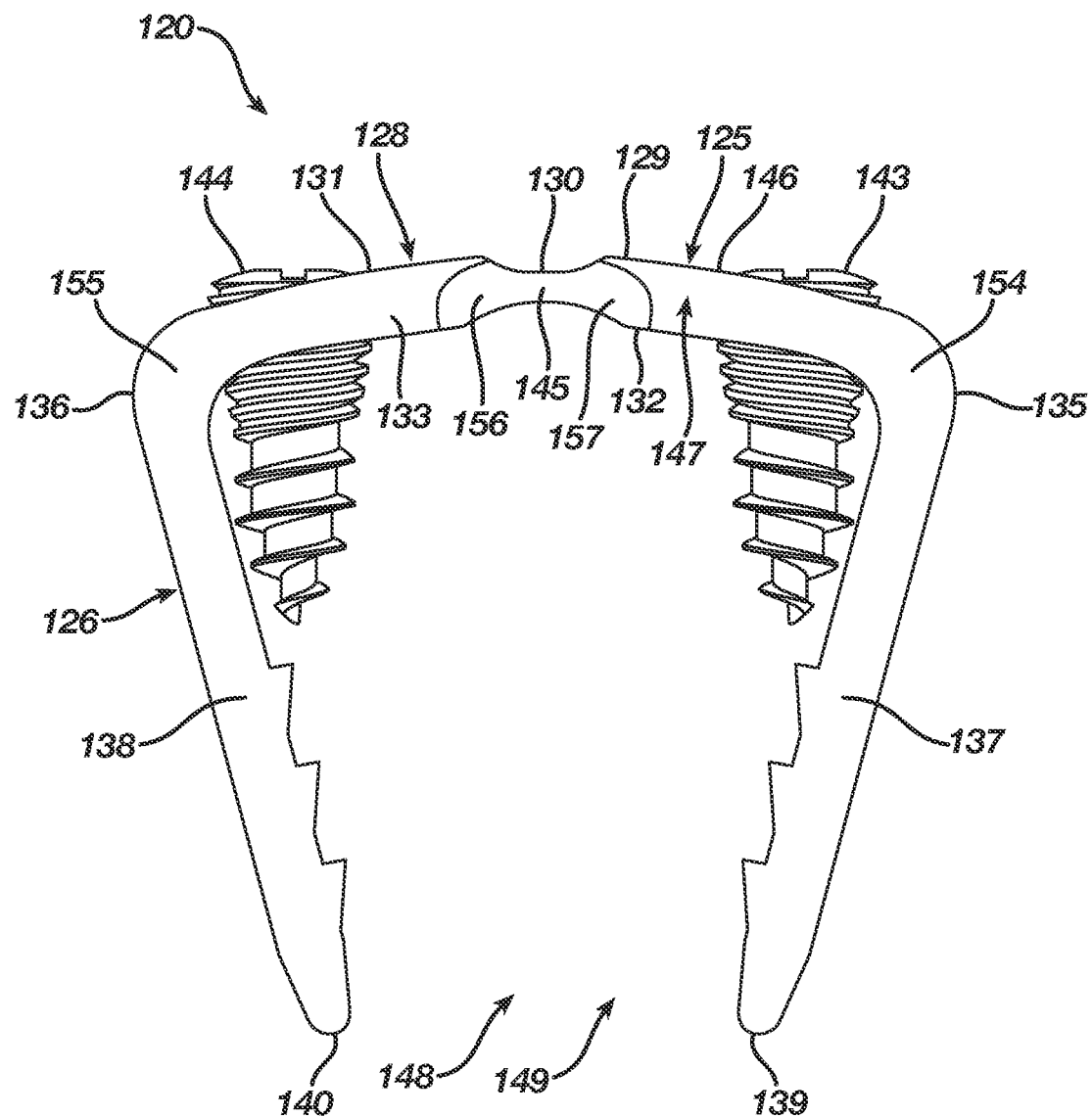
FIG. 9C is a front view illustrating the sternal closure system according to the third embodiment whereby the implant thereof resides in its natural shape and screws thereof engage the implant.
Figure 10A:
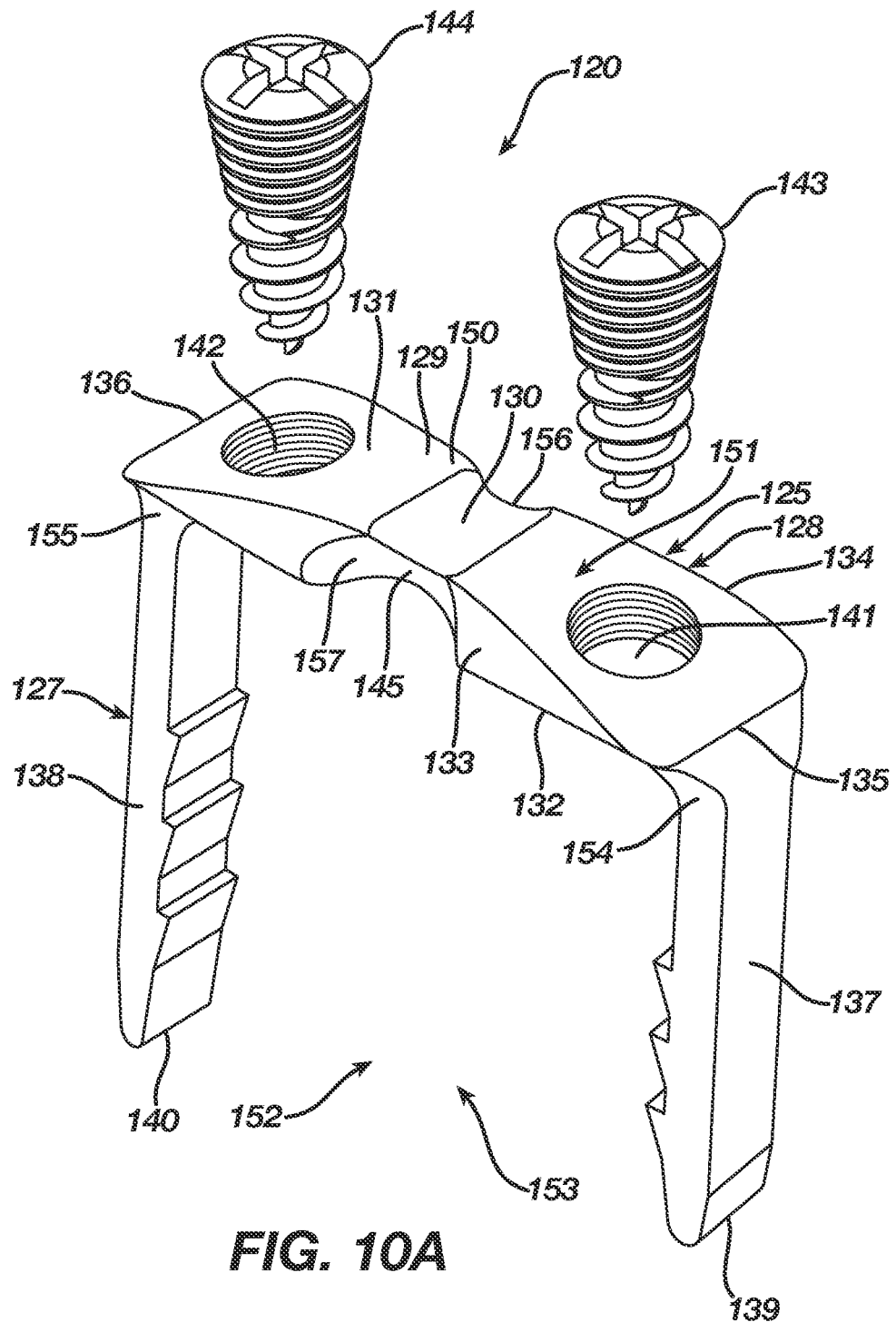
FIG. 10A is an isometric view illustrating the sternal closure system according to the third embodiment whereby the implant thereof resides in an insertion shape and screws thereof reside exterior of the implant.
Figure 10B:
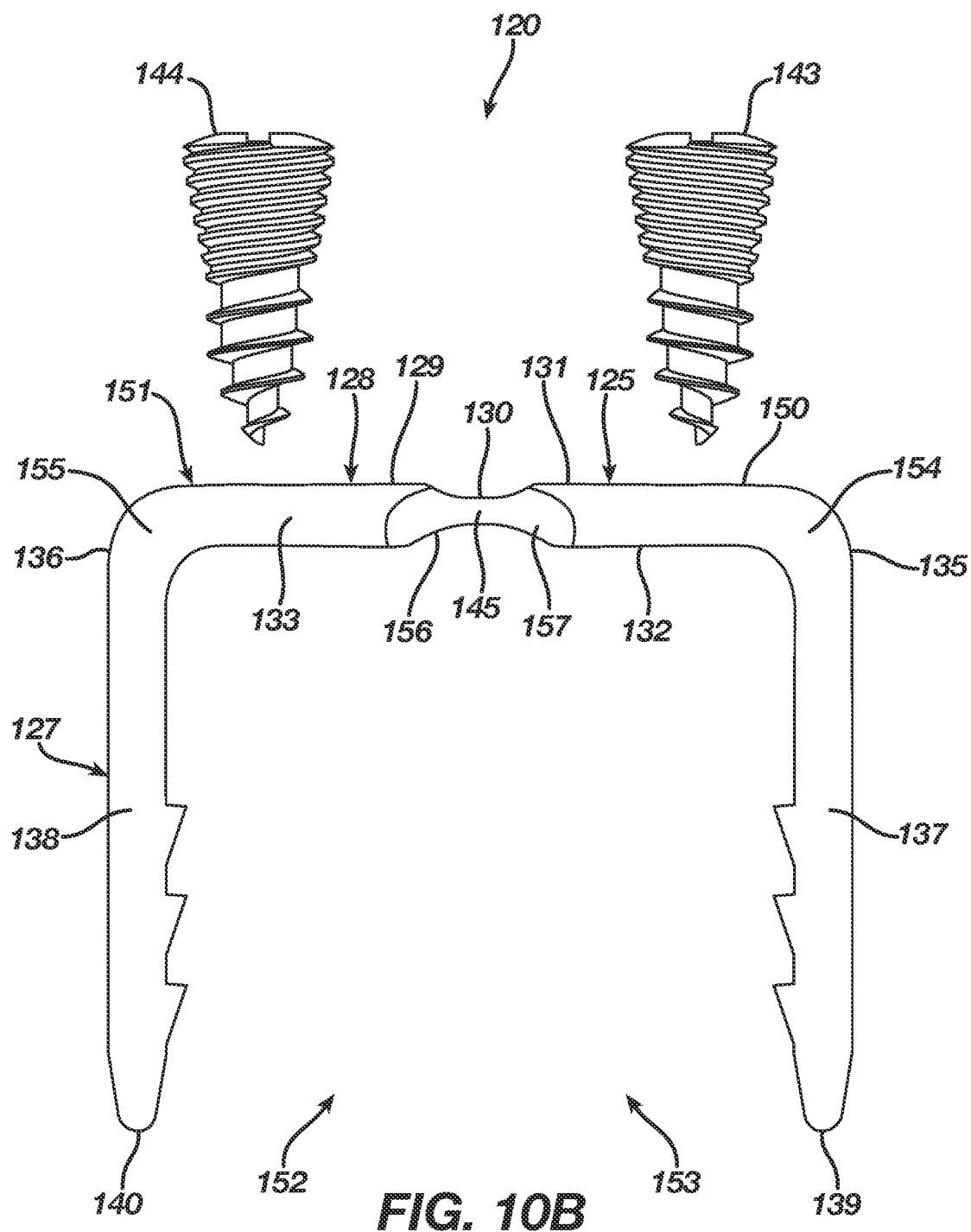
FIG. 10B is a front view illustrating the sternal closure system according to the third embodiment whereby the implant thereof resides in its insertion shape and screws thereof reside exterior of the implant.

As illustrated in FIGS. 9A-9C and 10A-10B, a sternal closure system 120 according to a third embodiment includes one or more orthopedic implants 125. FIGS. 9A-9C illustrate the implant 125 according to the sternal closure system 120 of the third embodiment in a natural shape 126, whereas FIGS. 10A-10B illustrate the implant 125 in an insertion shape 127. The implant 125 in the third embodiment of the sternal closure system 120 may be manufactured from a shape memory material with superelastic or temperature dependent properties (e.g., Nitinol) such that the implant 125 transitions between its natural shape 126 and its insertion shape 127. The implant 125 when deformed from its natural shape 126 to its insertion shape 127 stores energy deliverable to bone, bones, or bone pieces, and, in particular, to a thoracic wall. In accordance with its manufacture from shape memory material, the implant 125 begins in its natural shape 126, is transitionable to its insertion shape 127, and, once implanted in a thoracic wall, attempts to transition from its insertion shape 127 to its natural shape 126 whereby the implant 125 delivers the energy stored therein to the thoracic wall. More particularly, the implant 125 delivers the energy stored therein to a sternum of the thoracic wall across an opening created in the sternum thereby affixing the opening in the sternum closed and promoting a healing thereof. In the sternal closure system 120 according to the third embodiment, attempted transition of the implant 125 from its insertion shape 127 to its natural shape 126 continuously compresses the sternum in order to promote fusion thereof at the opening formed therein.

In the sternal closure system 120 according to the third embodiment, the implant 125 includes a bridge 128 with a length 129 and having a central axis 130. The bridge 128 in the third embodiment of the sternal closure system 120 is three-dimensional in form having a length, width, and height, and, in particular, an upper surface 131 and a lower surface 132 with first and second sides 133 and 134 and first and second ends 135 and 136 therebetween. The bridge 128 is tapered to present a non-uniform cross-sectional thickness between the upper and lower surfaces 131 and 132 in order to provide strength to the bridge 128 while lowering its profile. Although the bridge 128 is tapered in the third embodiment of the sternal closure system 120, one of ordinary skill in the art will recognize that the bridge 128 may include a uniform cross-sectional thickness between the upper and lower surfaces 131 and 132.

The implant 125 includes a first leg 137 extending from the bridge 128 at the first end 135 thereof and a second leg 138 extending from the bridge 128 at the second end 136 thereof. The first leg 137, which has a respective tip 139, may include barbs thereon that improve the pull-out resistance of the implant 12. Likewise, the second leg 138, which has a respective tip 140, may include barbs thereon that improve the pull-out resistance of the implant 125.

The bridge 128 includes a first aperture 141 therethrough that, in the sternal closure system 120 according to the third embodiment, is threaded and receives therethrough a fixation device 143. The fixation device 143 may be any suitable biocompatible metal screw, such as, for example, titanium, including a non-locking bone screw, a locking bone screw, and a self-tapping bone screw. The first aperture 141 is positioned from the central axis 130 lengthwise along the bridge 128 to a location adjacent the first leg 137 at the first end 135 of the bridge 128. The first aperture 141 may be positioned lengthwise along the bridge 128 to any location between the central axis 130 and the first end 135 of the bridge 128 provided the fixation device 143 when inserted into the first aperture 141 does not interfere with the first leg 137 when the implant 125 resides in its natural shape 126. Likewise, the bridge 128 includes a second aperture 142 therethrough that, in the sternal closure system 120 according to the third embodiment, is threaded and receives therethrough a fixation device 144. The fixation device 144 may be any suitable biocompatible metal screw, such as, for example, titanium, including a non-locking bone screw, a locking bone screw, and a self-tapping bone screw. The second aperture 142 is positioned from the central axis 130 lengthwise along the bridge 128 to a location adjacent the second leg 138 at the second end 136 of the bridge 128. The second aperture 142 may be positioned lengthwise along the bridge 128 to any location between the central axis 130 and the second end 136 of the bridge 128 provided the fixation device 144 when inserted into the second aperture 142 does not interfere with the second leg 138 when the implant 125 resides in its natural shape 126. The first aperture 141 and the first leg 137 and the second aperture 142 and the second leg 138 accordingly are aligned lengthwise along the bridge 128 such that the first and second apertures 141 and 142 are spaced apart at a first distance and the first and second legs 137 and 138 are spaced apart at a second distance that is greater than the first distance.

The bridge 128 includes a transition section 145 disposed at the central axis 130 thereof. The natural shape 126 of the implant 125, as illustrated in FIGS. 9A-9B, involves the transition section 145 locating the bridge 128 in a natural form 146 which, in the sternal closure system 120 according to the third embodiment, is a closed or angular profile whereby the first and second ends 135 and 136 reside at a first distance 147 and the first and second legs 137 and 138 reside in a natural position 148, which is convergent whereby the first and second legs 137 and 138 are spaced apart at a first distance 149. Nevertheless, as illustrated in FIGS. 10A and 10B, the implant 125 is deformable under the action of superelasticity or shape memory temperature dependent properties to an insertion shape 127 where the transition section 145 deforms to store energy while also moving the bridge 128 from its natural form 146 to an insertion form 150 which, in the sternal closure system 120 according to the third embodiment, is an open or substantially linear profile whereby the first and second ends 135 and 136 reside at a second distance 151 that is greater than the first distance 147 and the first and second legs 137 and 138 reside in an insertion position 152, which is substantially parallel whereby the first and second legs 137 and 138 are spaced apart at a second distance 153 that is greater than the first distance 149. Since the insertion shape 127 is not the natural shape 126 of the implant 125, the implant 125 at the transition section 145 and/or the first and second legs 137 and 138 typically is mechanically constrained or the implant 125 is chilled until the implant 125 reaches its martensite phase whereby the transition section 145 once deformed maintains the bridge 128 in its insertion form 150 and the first leg 137 and the second leg 138 in their insertion position 152. A release of a mechanical constraint or a heating of the implant 125 to its austenite phase results in the implant 125 delivering the energy stored in the transition section 145 such that the bridge 128 attempts to transition from its insertion form 150 to its natural form 146 resulting in the first and second legs 137 and 138 attempting to move from their insertion position 152 to their natural position 148 thereby exerting a compressive force after implantation into a sternum across an opening formed therein. Mechanical constraints suitable to engage the implant 125 and maintain the implant 125 in its insertion shape 127 are available from DePuy Synthes Products, Inc., 325 Paramount Drive, Rayham, Mass. 02767, and include forceps, pliers, and implant insertion devices, such as, for example, the implant insertion devices disclosed in U.S. Pat. Nos. 9,585,656 B2 and 10,456,131 B2.

Alternatively, the bridge 128 in the sternal closure system 120 according to the third embodiment may include a first transition section 154 located where the first leg 137 extends from the bridge 128 and a second transition section 155 located where the second leg 138 extends from the bridge 128. The natural shape 126 of the implant 125, as illustrated in FIGS. 9A-9C, involves the first and second transition sections 154 and 155, respectively, locating the first leg 137 and the second leg 138 in a natural position, which, in the sternal closure system 120 according to the third embodiment, is convergent whereby the first leg 137 and the second leg 138 are spaced apart at a first distance. Nevertheless, the implant 125 is deformable under the action of superelasticity or temperature dependent shape memory properties to an insertion shape where the first and second transition sections 154 and 155 deform to store energy while also moving, respectively, the first leg 137 and the second leg 138 to an insertion position, which, in the sternal closure system 120 according to the third embodiment, is substantially parallel whereby the first leg 137 and the second leg 138 are spaced apart at a second distance that is greater than the first distance. FIGS. 10A-10B illustrated the insertion shape of the implant 125 and the insertion position of the first and second legs 137 and 138 with the exception that the bridge 128 would include the closed or angular profile illustrated in FIGS. 9A-9C. Since the insertion shape is not the natural shape 126 of the implant 125, the implant 125 at the first and second transition sections 154 and 155 typically is mechanically constrained or the implant 125 is chilled until the implant 125 reaches its martensite phase whereby the first and second transition sections 154 and 155 once deformed maintain the first leg 137 and the second leg 138 in their insertion position. A release of a mechanical constraint or a heating of the implant 125 to its austenite phase results in the implant 125 delivering the energy stored in the first and second transition sections 154 and 155 such that the first leg 137 and the second leg 138 attempt to move from their insertion position to their natural position thereby exerting a compressive force after implantation into a sternum across an opening formed therein. Mechanical constraints suitable to engage the implant 125 and maintain the implant 125 in its insertion shape are available from DePuy Synthes Products, Inc., 325 Paramount Drive, Rayham, Mass. 02767, and include forceps, pliers, and implant insertion devices, such as, for example, the implant insertion devices disclosed in U.S. Pat. Nos. 9,585,656 B2 and 10,456,131 B2.

Although the implant 125 has been described as including either the transition section 145 or the first and second transition sections 154 and 155 to produce deformation thereof, one of ordinary skill in the art will recognize that the bridge 128 of the implant 125 may include both the transition section 145 and the first and second transition section 154 and 155 to produce deformation thereof. Moreover, while the bridge 128 includes a closed or angular profile in the natural shape 126 of the implant 125, it should be understood by one of ordinary skill in the art that, when the bridge 128 incorporates the first and second transition sections 154 and 155, the bridge 128 as illustrated in FIGS. 10A and 10B may include an open or substantially linear profile in a natural shape of the implant 125. Furthermore, the bridge 128 maintains its open or substantially linear profile once the implant 125 deforms to an insertion shape.

Even though it is important for the implant 125 to compress a sternum and hold closed an opening therein while remaining securely fastened with the sternum, the implant 125 in an emergency situation requiring an intervention through the sternum should allow quick and easy re-opening of the sternum at the opening. In accordance therewith, the implant 125 at the central axis 130 of the bridge 128 includes a groove 156 that removes material from the bridge 128, resulting in the bridge 128 having a reduced cross-section 157 that facilitates quick and easy cutting of the bridge 128 at the groove 156. In the sternal closure system 120 according to the third embodiment, the groove 156 traverses the bridge 128 about its upper and lower surfaces 131 and 132 and its first and second sides 133 and 134. If an emergency situation arises requiring an intervention through the sternum, the implant 125 is cut at the groove 156 using a suitable instrument, such as, for example, trauma shears. The implant 125, due to the cutting thereof, releases the sternum thereby allowing re-access to a thoracic cavity via the sternum and a re-opened opening therein.

The implant 125 in the sternal closure system 120 according to the third embodiment may include multiple variations whereby a length 129 of the bridge 130 and lengths of the first and second legs 137 and 138 of one version are different from the lengths 129 of the bridges 128 and the lengths of the first and second legs 137 and 138 of other versions. The length 129 of the bridge 128 for a version of the implant 125 is determined based upon a bridge size requirement necessary for the implant 125 to span a sternum and achieve a closure of an opening formed in the sternum. Moreover, the lengths of the first and second legs 137 and 138 for a version of the implant 125 is determined based upon a leg seating requirement necessary for the implant 125 to insert into a thoracic wall at an outer cortex thereof and then fixate in the thoracic wall without undue extension of the first and second legs 137 and 138 into the thoracic wall.

Figure 11B:
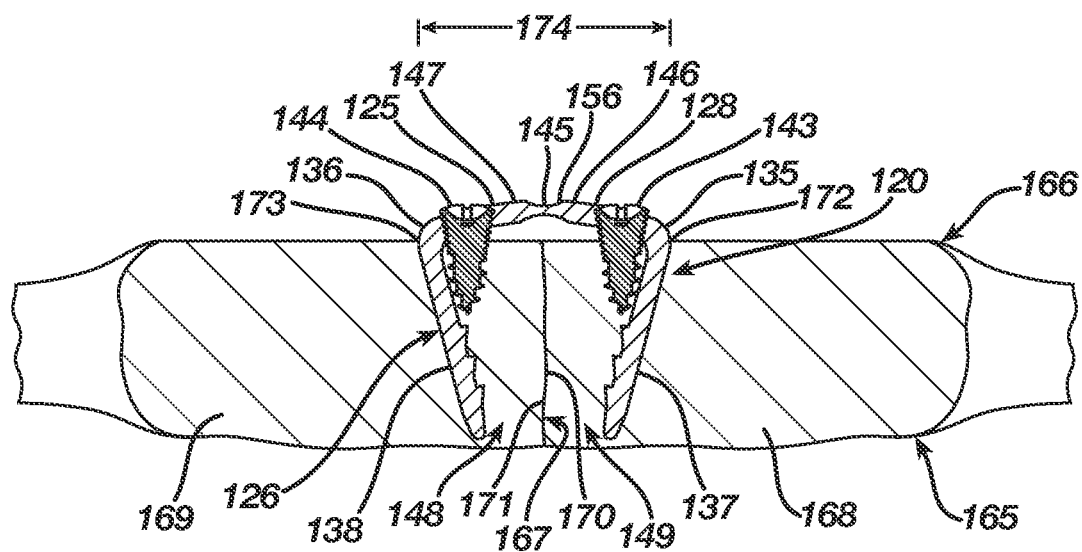
FIG. 11B is a cross-sectional view taken along lines C-C of FIG. 11A illustrating the sternal closure system according to the third embodiment as utilized in closing a sternum whereby the implant thereof attempts transition to its natural shape and the screws thereof engage the implant.

FIGS. 11A-11B illustrate the sternal closure system 120 according to the third embodiment as utilized during a surgery involving access into a thoracic cavity 164 through a thoracic wall 165. In addition to the configuration of the plurality of implants shown with respect to the vertical sternotomy illustrated in FIGS. 11A-11B, one of ordinary skill in the art can envision alternate implant arrangements that can accommodate, for example, one or more mini-sternotomies, transverse sternotomies, and J-cut sternotomies, and combinations thereof. Such alternate implant configurations may include any number of arrangements of the implants with respect to one another, such as perpendicular, parallel, or transverse arrangements, or combinations thereof. To access the thoracic cavity 164, a sternum 166 of the thoracic wall 165 is perforated thereby forming therein an opening 167 through which the thoracic cavity 164 is accessed. The perforation of the sternum 166 through the forming of the opening 167 therein creates a first segment 168 and a second segment 169 in the sternum 166, while the opening 167 includes a first side 170 and a second side 171. Upon completion of the surgery, the thoracic wall 165, and, in particular, the sternum 166 at its first and second segments 168 and 169, is manipulated such that the opening 167 closes along its first and second sides 170 and 171 and then is held closed using a suitable device or devices, such as, for example, a clamp or clamps.

With the opening 167 in the sternum 166 held closed, one or more sternal closure systems 120 according to the third embodiment are secured with the thoracic wall 165 in order to maintain the opening 167 in the sternum 166 closed. More particularly, an implant 125 implanted into the sternum 166 across the opening 167 holds the opening 167 in the sternum 166 closed along its first and second sides 170 and 171 and promotes a healing of the sternum 166 at the opening 167 therein. Illustratively, a first hole 172 created to assist in the insertion of the first leg 137 of the implant 125 is drilled into the first segment 168 of the sternum 166, whereas a second hole 173 created to assist in the insertion of the second leg 138 of the implant 125 is drilled into the second segment 169 of the sternum 166. The first hole 172 and the second hole 173 are separated a distance 174 substantially equal to the second distance 153 between the first leg 137 and the second leg 138 of the implant 125 when the first and second legs 137 and 138 reside in their insertion position 152. The implant 125, while held, for example, by an implant insertion device, in its insertion shape 127 whereby the first leg 137 and the second leg 138 in their insertion position 152 are spaced apart the second distance 153, is introduced into the first segment 168 of the sternum 166 via the first hole 172 and the second segment 169 of the sternum 166 via the second hole 173. The implant 125, and, more particularly, the first and second legs 137 and 138, respectively, due to the distance 174 between the first and second holes 172 and 173 being substantially equal to the second distance 153 of the first and second legs 137 and 138 in their insertion position 152, insert into the first and second holes 172 and 173. The first leg 137 inserts into the first segment 168 of the sternum 166 via the first hole 172 until the bridge 128 at the first end 135 thereof resides atop and contacts the first segment 168 of the sternum 166. Likewise, the second leg 138 inserts into the second segment 169 of the sternum 166 via the second hole 173 until the bridge 128 at the second end 136 thereof resides atop and contacts the second segment 169 of the sternum 166. While the first and second holes 172 and 173 assist in the insertion of the implant 125 into the sternum 166, one of ordinary skill in the art will recognize that the implant 125 may be implanted into the sternum 166 across the opening 167 therein through impaction of the first and second legs 137 and 138, respectively, into the first and second segments 168 and 169 of the sternum 166.

With the first leg 137 inserted into the first segment 168 of the sternum 166 and the second leg 138 inserted into the second segment 169 of the sternum 166, the implant 125 is released, which, by way of example, involves disengaging the implant insertion device from the implant 125. After release of the implant 125, the implant 125 at its bridge 128, if necessary, may be tamped until the bridge 128 at its first and second ends 135 and 136, respectively, resides atop and contacts the first and second segments 168 and 169 of the sternum 166. The released implant 12, due to its superelasticity or a heating thereof, delivers the energy stored in its transition section 145 (or first and second transition sections 154 and 155), resulting in the implant 125 attempting to transition from its insertion shape 127 to its natural shape 126 whereby the bridge 128 attempts to transition from its insertion form 150 to its natural form 146 resulting in the first and second legs 137 and 138 attempting to move from their insertion position 152 to their natural position 148. The implant 125, consequently, exerts a compressive force to the sternum 166 at the first and second segments 168 and 169 across the opening 167 therein. The first leg 137 and the second leg 138, accordingly, engage the sternum 166 at an outer cortex thereof in order to fixate the implant 125 with its bridge 128 traversing the sternum 166 at the opening 167 such that the implant 125 holds the opening 167 closed at its first and second sides 170 and 171.

While the implant 125 exerts the compressive force to the sternum 166 across the opening 167 thereby holding the opening 167 closed, the implant 125 further includes the first and second apertures 141 and 142 to assist in maintaining the implant 125 fastened with the sternum 166 whereby the implant 125 is not subject to a movement about the sternum 166, a loosening relative to the sternum 166, or a dislodgement from the sternum 166 that causes a re-opening of the sternum 106 at the opening 107. Illustratively, a fixation device 143, which may be self-tapping bone screw, inserts into the bridge 128 of the implant 125 through the first aperture 141 and engages the first segment 168 of the sternum 166. The fixation device 143 enters the first segment 168 of the sternum 166 until the fixation device 143 seats substantially, completely within the first aperture 141. Likewise, a fixation device 144, which may be self-tapping bone screw, inserts into the bridge 128 of the implant 125 through the second aperture 142 and engages the second segment 169 of the sternum 166. The fixation device 144 enters the second segment 169 of the sternum 166 until the fixation device 144 seats substantially, completely within the second aperture 142. The fixation devices 143 and 144 engage the sternum 166 at an outer cortex thereof in order to fixate the bridge 128 of the implant 125 atop the first and second segments 168 and 169 of the sternum 166. The engagement of the bridge 128 with the sternum 166 across the opening 167 via the fixation devices 143 and 144 and their respective insertion at the first and second apertures 141 and 142 of the bridge 128 assists the first and second legs 137 and 138 in affixing the implant 125 with the sternum 166 such that the implant 125 remains secured with the sternum 166 and is not subject to movement, loosening, or dislodgement.

Alternatively, a hole created to assist in the insertion of the fixation device 143, which may be a non-locking or locking bone screw, may be drilled into the first segment 168 of the sternum 166 at the first aperture 141 of the bridge 128. The fixation device 143 inserts into the bridge 128 of the implant 125 through the first aperture 141 and then into the first segment 168 of the sternum 166 via the hole such that the fixation device 143 engages the first segment 168 of the sternum 166. The fixation device 143 enters the first segment 168 of the sternum 166 until the fixation device 143 seats substantially, completely within the first aperture 141. Likewise, a hole created to assist in the insertion of the fixation device 144, which may be a non-locking or locking bone screw, may be drilled into the second segment 169 of the sternum 166 at the second aperture 142 of the bridge 128. The fixation device 144 inserts into the bridge 128 of the implant 125 through the second aperture 142 and then into the second segment 169 of the sternum 166 via the hole such that the fixation device 144 engages the second segment 169 of the sternum 166. The fixation device 144 enters the second segment 169 of the sternum 166 until the fixation device 144 seats substantially, completely within the second aperture 142. The fixation devices 143 and 144 engage the sternum 166 at an outer cortex thereof in order to fixate the bridge 128 of the implant 125 atop first and second segments 168 and 169 of the sternum 166. The engagement of the bridge 128 with the sternum 166 across the opening 167 via the fixation devices 143 and 144 and their respective insertion at the first and second apertures 141 and 142 of the bridge 128 assists the first and second legs 137 and 138 in affixing the implant 125 with the sternum 166 such that the implant 125 remains secured with the sternum 166 and is not subject to movement, loosening, or dislodgement.

Even though a single sternal closure system 120 according to the third embodiment will hold closed the opening 167 in the sternum 166, an additional sternal closure system 120 or sternal closure systems 120 may be secured with the sternum 166 across the opening 167. The additional sternal closure systems 120 secure with the sternum 166 across the opening 167 as previously described with reference to the single sternal closure system 120. Once the one or more sternal closure systems 120 secure with the sternum 166 across the opening 167, any clamps holding the sternum 166 closed are removed in order to permit completion of the surgery. The one or more sternal closure systems 120 secured with the sternum 166 across the opening 167 may remain after the surgery or alternatively may be removed at a later date after a healing of the sternum 166.

Although the one or more implants 125 compress the sternum 166 at the opening 167 while remaining securely fastened therewith, each implant 125 in an emergency situation requiring an intervention through the sternum 166 may be quickly removed by a cutting of the implant 125 at the groove 156 using a suitable instrument, such as, for example, trauma shears. The implant 125, due to the cutting thereof, releases the sternum thereby allowing re-access to a thoracic cavity via the sternum and a re-opened opening therein.

A feature of the sternal closure system 120 according to the third embodiment includes its use in combination with one or both of the sternal closure systems 10 and 50 according to the first and second embodiments. The sternal closure systems 10, 50, and 120 according to the first, second, and third embodiments each may be secured with a thoracic wall as previously described in order to maintain an opening in a sternum closed.

The sternal closure systems 10, 50, and 120 according to the first, second, and third embodiments provide improvements in sternal closure on the basis the sternal closure systems 10, 50, and 120 achieve a desired sternal closure while remaining flexible to account for thoracic wall movement and further are quickly removable in the event acute re-entry through a sternum becomes necessary. In particular, the implants 12 and 120, due to their construction from a shape memory material, are pliable and thus deformable such that the implants 12 and 120 flex during normal thoracic wall movement, including movement created through breathing, whereby the sternal closure systems 10, 50, and 120 are unlikely to penetrate into the thoracic wall. Moreover, the flexibility of the implants 12 and 120 is likely to prevent a movement of the sternal closure systems 10, 50, and 120 about the sternum, a loosening of the sternal closure systems 10, 50, and 120 relative to the sternum, or a dislodgement of the sternal closure systems 10, 50, and 120 from the sternum that causes a re-opening of the sternum.

Still further, as previously described, the implants 12 and 120 facilitate a rapid re-entry through a sternum if necessary.

In view of the foregoing embodiments illustrating the sternal closure systems according to the present invention, it should be understood that a sternal closure system will fall within the scope of the present invention regardless of the shape or number of apertures for the first and second plates and the shape or size of the implants. Moreover, although the present invention has been described in terms of the foregoing embodiments, such description has been for exemplary purposes only and, as will be apparent to those of ordinary skill in the art, many alternatives, equivalents, and variations of varying degrees will fall within the scope of the present invention. That scope, accordingly, is not to be limited in any respect by the foregoing detailed description; rather, it is defined only by the claims that follow.

The invention claimed is:

1. A sternal closure system adapted for closing an opening in a sternum of a thoracic wall, comprising:
   an implant moveable between a natural shape and an insertion shape;
   a first plate adapted for receiving the implant therethrough, the first plate being adapted for securing with the sternum adjacent a first side of the opening;
   a second plate adapted for receiving the implant therethrough, the second plate being adapted for securing with the sternum adjacent a second side of the opening;
   the implant, when positioned in the insertion shape, being adapted to insert through the first plate and the second plate and into the sternum across the opening; and
   the implant, upon a movement thereof from the insertion shape toward the natural shape, being adapted to hold the opening in the sternum closed while interconnecting the first plate and the second plate.

2. The sternal closure system of claim 1, wherein:
   the first plate includes a first end and a second end, a first side and a second side, a first aperture extending through the first plate at the first end, and a second aperture adjacent the first aperture extending through the first plate; and
   the second plate includes a first end and a second end, a first side and a second side, a first aperture extending through the second plate at the first end, and a second aperture adjacent the first aperture extending through the second plate.

3. The sternal closure system of claim 2, the implant, comprising:
   a bridge with a first end and a second end and having a length;
   a first leg extending from the bridge;
   a second leg extending from the bridge, wherein the first leg and the second leg reside in a natural position at a first distance when the implant is positioned in the natural shape and the first leg and the second leg reside in an insertion position at a second distance when the implant is positioned in the insertion shape.

4. The sternal closure system of claim 3, wherein:
   the first aperture of the first plate and the second plate is configured to receive therethrough one of a fixation device and one of the first leg and the second leg of the implant; and
   the second aperture of the first plate and the second plate is configured to receive therethrough one of a fixation device and one of the first leg and the second leg of the implant.

5. The sternal closure system of claim 4, wherein:

the first plate includes a first slot extending from the first aperture to the first side and a second slot extending from the second aperture to the first side, the first and second slots being configured to receive therein the bridge of the implant at one of the first end and the second end of the bridge whereby the first and second slots permit seating of the implant within the first plate; and the second plate includes a first slot extending from the first aperture to the first side and a second slot extending from the second aperture to the first side, the first and second slots being configured to receive therein the bridge of the implant at one of the first end and the second end of the bridge whereby the first and second slots permit seating of the implant within the second plate.

6. The sternal closure system of claim 5, wherein:

the first plate being adapted for securing with the sternum adjacent the first side of the opening using a fixation device inserted through the first aperture and into the sternum;

the second plate being adapted for securing with the sternum adjacent the second side of the opening using a fixation device inserted through the first aperture and into the sternum;

the first plate and the second plate being oriented substantially parallel whereby the second slot of the first plate aligns with the second slot of the second plate and the second aperture of the first plate and the second aperture of the second plate are aligned and separated across the opening by a distance substantially equal to the second distance of the first leg and the second leg in the insertion position;

the implant, when positioned in the insertion shape with the first leg and the second leg in the insertion position at the second distance, being adapted whereby the first leg of the implant inserts through the second aperture of the first plate and into the sternum and the second leg of the implant inserts through the second aperture of the second plate and into the sternum until the bridge of the implant seats at the first end in the second slot of the first plate and at the second end in the second slot of the second plate such that the bridge spans the opening; and the implant, upon a movement thereof from the insertion shape toward the natural shape, being adapted whereby the implant holds the opening in the sternum closed while the first leg engages the first plate and the second leg engages the second plate such that the implant interconnects the first plate and the second plate.

7. The sternal closure system of claim 4, wherein:

the first plate includes a first countersink at the first aperture and a second countersink at the second aperture, the first and second countersinks being configured to receive therein a fixation device whereby the first and second countersinks permit seating of the fixation device within the first plate; and the second plate includes a first countersink at the first aperture and a second countersink at the second aperture, the first and second countersinks being configured to receive therein a fixation device whereby the first and second countersinks permit seating of the fixation device within the second plate.

8. The sternal closure system of claim 4, wherein:

the first plate being adapted for securing with the sternum adjacent the first side of the opening using a fixation device inserted through the first aperture and into the sternum;

the second plate being adapted for securing with the sternum adjacent the second side of the opening using a fixation device inserted through the first aperture and into the sternum;

the second aperture of the first plate and the second aperture of the second plate being aligned and separated across the opening by a distance substantially equal to the second distance of the first leg and the second leg in the insertion position;

the implant, when positioned in the insertion shape with the first leg and the second leg in the insertion position at the second distance, being adapted whereby the first leg of the implant inserts through the second aperture of the first plate and into the sternum and the second leg of the implant inserts through the second aperture of the second plate and into the sternum such that the bridge of the implant spans the opening; and the implant, upon a movement thereof from the insertion shape toward the natural shape, being adapted whereby the implant holds the opening in the sternum closed while the first leg engages the first plate and the second leg engages the second plate such that the implant interconnects the first plate and the second plate.

9. The sternal closure system of claim 4, wherein:

the first plate includes a third aperture adjacent the second aperture extending through the first plate, the third aperture being configured to receive therethrough one of a fixation device and one of the first leg and the second leg of the implant; and the second plate includes a third aperture adjacent the second aperture extending through the second plate, the third aperture being configured to receive therethrough one of a fixation device and one of the first leg and the second leg of the implant.

10. The sternal closure system of claim 9, wherein:

the first plate being adapted for securing with the sternum adjacent the first side of the opening using a fixation device inserted through the first aperture and into the sternum and a fixation device inserted through the third aperture and into the sternum;

the second plate being adapted for securing with the sternum adjacent the second side of the opening using a fixation device inserted through the first aperture and into the sternum and a fixation device inserted through the third aperture and into the sternum;

the second aperture of the first plate and the second aperture of the second plate being aligned and separated across the opening by a distance substantially equal to the second distance of the first leg and the second leg in the insertion position;

the implant, when positioned in the insertion shape with the first leg and the second leg in the insertion position at the second distance, being adapted whereby the first leg of the implant inserts through the second aperture of the first plate and into the sternum and the second leg of the implant inserts through the second aperture of the second plate and into the sternum such that the bridge of the implant spans the opening; and the implant, upon a movement thereof from the insertion shape toward the natural shape, being adapted whereby the implant holds the opening in the sternum closed while the first leg engages the first plate and the second leg engages the second plate such that the implant interconnects the first plate and the second plate.

11. The sternal closure system of claim 3, wherein:
the first aperture of the first plate and the second plate is configured to receive therethrough one of the first leg and the second leg of the implant; and
the second aperture of the first plate and the second plate is configured to receive therethrough a fixation device.

12. The sternal closure system of claim 11, wherein:
the first plate includes a slot extending from the first aperture to the first end, the slot being configured to receive therein the bridge of the implant at one of the first end and the second end of the bridge whereby the slot permits seating of the implant within the first plate; and
the second plate includes a slot extending from the first aperture to the first end, the slot being configured to receive therein the bridge of the implant at one of the first end and the second end of the bridge whereby the slot permits seating of the implant within the second plate.

13. The sternal closure system of claim 12, wherein:
the first plate being adapted for securing with the sternum adjacent the first side of the opening using a fixation device inserted through the second aperture and into the sternum;
the second plate being adapted for securing with the sternum adjacent the second side of the opening using a fixation device inserted through the second aperture and into the sternum;
the first plate and the second plate being oriented substantially perpendicular whereby the slot of the first plate aligns with the slot of the second plate and the first aperture of the first plate and the first aperture of the second plate are aligned and separated across the opening by a distance substantially equal to the second distance of the first leg and the second leg in the insertion position;
the implant, when positioned in the insertion shape with the first leg and the second leg in the insertion position at the second distance, being adapted whereby the first leg of the implant inserts through the first aperture of the first plate and into the sternum and the second leg of the implant inserts through the first aperture of the second plate and into the sternum until the bridge of the implant seats at the first end in the slot of the first plate and at the second end in the slot of the second plate such that the bridge spans the opening; and
the implant, upon a movement thereof from the insertion shape toward the natural shape, being adapted whereby the implant holds the opening in the sternum closed while the first leg engages the first plate and the second leg engages the second plate such that the implant interconnects the first plate and the second plate.

14. The sternal closure system of claim 11, wherein:
the first plate includes a countersink at the second aperture, the countersink being configured to receive therein a fixation device whereby the countersink permits seating of the fixation device within the first plate; and
the second plate includes a countersink at the second aperture, the countersink being configured to receive therein a fixation device whereby the countersink permits seating of the fixation device within the second plate.

15. The sternal closure system of claim 11, wherein:
the first plate being adapted for securing with the sternum adjacent the first side of the opening using a fixation device inserted through the second aperture and into the sternum;
the second plate being adapted for securing with the sternum adjacent the second side of the opening using a fixation device inserted through the second aperture and into the sternum;
the first aperture of the first plate and the first aperture of the second plate being aligned and separated across the opening by a distance substantially equal to the second distance of the first leg and the second leg in the insertion position;
the implant, when positioned in the insertion shape with the first leg and the second leg in the insertion position at the second distance, being adapted whereby the first leg of the implant inserts through the first aperture of the first plate and into the sternum and the second leg of the implant inserts through the first aperture of the second plate and into the sternum such that the bridge of the implant spans the opening; and
the implant, upon a movement thereof from the insertion shape toward the natural shape, being adapted whereby the implant holds the opening in the sternum closed while the first leg engages the first plate and the second leg engages the second plate such that the implant interconnects the first plate and the second plate.

16. The sternal closure system of claim 11, wherein:
the first plate includes a third aperture adjacent the second aperture extending through the first plate, the third aperture being configured to receive therethrough a fixation device; and
the second plate includes a third aperture adjacent the second aperture extending through the second plate, the third aperture being configured to receive therethrough a fixation device.

17. The sternal closure system of claim 16, wherein:
the first plate being adapted for securing with the sternum adjacent the first side of the opening using a fixation device inserted through the second aperture and into the sternum and a fixation device inserted through the third aperture and into one of the sternum and a rib of the thoracic wall;
the second plate being adapted for securing with the sternum adjacent the second side of the opening using a fixation device inserted through the second aperture and into the sternum and a fixation device inserted through the third aperture and into one of the sternum and a rib of the thoracic wall;
the first aperture of the first plate and the first aperture of the second plate being aligned and separated across the opening by a distance substantially equal to the second distance of the first leg and the second leg in the insertion position;
the implant, when positioned in the insertion shape with the first leg and the second leg in the insertion position at the second distance, being adapted whereby the first leg of the implant inserts through the first aperture of the first plate and into the sternum and the second leg of the implant inserts through the first aperture of the second plate and into the sternum such that the bridge of the implant spans the opening; and
the implant, upon a movement thereof from the insertion shape toward the natural shape, being adapted whereby the implant holds the opening in the sternum closed while the first leg engages the first plate and the second leg engages the second plate such that the implant interconnects the first plate and the second plate.

18. A sternal closure system adapted for closing an opening in a sternum of a thoracic wall, comprising:
a plurality of implants, each being moveable between a natural shape and an insertion shape;
a plurality of plate pairs, comprising:
a plurality of first plates, each being adapted for receiving at least one of the plurality of implants therethrough, and each being adapted for securing along the sternum adjacent a first side of the opening,
a plurality of second plates, each being adapted for receiving at least one of the plurality of implants therethrough, and each being adapted for securing along the sternum adjacent a second side of the opening in alignment with one of the plurality of first plates, and
one of the plurality of first plates aligned across the opening with one of the plurality of second plates forming one of the plurality of plate pairs;
the plurality of implants, when positioned in the insertion shape, each being adapted to insert through one of the plurality of plate pairs and into the sternum across the opening; and
the plurality of implants, upon a movement from the insertion shape toward the natural shape, each being adapted to hold the opening in the sternum closed while interconnecting one of the plurality of plate pairs.

19. The sternal closure system of claim 18, the plurality of implants, each comprising:
a bridge with a first end and a second end and having a length;
a first leg extending from the bridge;
a second leg extending from the bridge, wherein the first leg and the second leg reside in a natural position at a first distance when the implant is positioned in the natural shape and the first leg and the second leg reside in an insertion position at a second distance when the implant is positioned in the insertion shape.

20. The sternal closure system of claim 19, the plurality of first plates and the plurality of second plates each including an aperture configured to receive therethrough one of the first leg and one of the second leg of the plurality of implants.

21. The sternal closure system of claim 20, wherein:
the plurality of plate pairs each being adapted for securing with the sternum across the opening whereby each aperture of the plurality of first plates and each aperture of the plurality of second plates aligns and is separated across the opening by a distance substantially equal to the second distance of the first leg and the second leg in the insertion position;
the plurality of implants, when positioned in the insertion shape with the first leg and the second leg in the insertion position at the second distance, each being adapted whereby the first leg inserts through the aperture of one of the plurality of first plates and into the sternum and the second leg of the implant inserts through the aperture of one of the of the plurality of second plates and into the sternum such that the bridge of the implant spans the opening; and
the plurality of implants, upon a movement from the insertion shape toward the natural shape, each being adapted whereby one of the plurality of implants holds the opening in the sternum closed while the first leg engages one of the plurality of first plates and the second leg engages one of the plurality of second plates such that the one of the plurality of implants interconnects one of the plurality of plate pairs.

22. A sternal closure system adapted for closing an opening in a sternum of a thoracic wall, comprising:
at least a first implant and a second implant, each of the first implant and the second implant being moveable between a natural shape and an insertion shape;
the first implant and the second implant, each comprising:
a bridge having a length and with a first end, a second end, and a central axis therebetween, the bridge being deformable between a natural form and an insertion form that transitions the first implant and the second implant between the natural shape and the insertion shape,
a first leg extending from the bridge at the first end,
a second leg extending from the bridge at the second end, whereby, when the bridge is positioned in the natural form, the first leg and the second leg reside in a natural position with the first leg and the second leg spaced apart at a first distance, further whereby, when the bridge is positioned in the insertion form, the first leg and the second leg reside in an insertion position with the first leg and the second leg spaced apart at a second distance greater than the first distance,
the bridge including:
a first aperture therethrough positioned from the central axis lengthwise along the bridge to a location between the central axis and the first leg, wherein the first aperture when the first leg resides in the natural position is adapted to receive a fixation device that secures the bridge with the sternum interior of the first leg, and
a second aperture therethrough positioned from the central axis lengthwise along the bridge to a location between the central axis and the second leg, wherein the second aperture when the second leg resides in the natural position is adapted to receive a fixation device that secures the bridge with the sternum interior of the second leg;
the first implant, when positioned in the insertion shape with the bridge in the insertion form and the first leg and the second leg in the insertion position at the second distance, being adapted to secure with the sternum across the opening at a first location, whereby the first leg inserts into the sternum adjacent a first side of the opening, the second leg inserts into the sternum adjacent a second side of the opening, and the bridge spans the opening;
the first implant, upon a movement thereof from the insertion shape toward the natural shape with the bridge moving toward the natural form and the first leg and the second leg moving toward the natural position, being adapted to hold the opening in the sternum closed at the first location, whereby the first aperture receives a fixation device therethrough that engages the sternum at the first side of the opening to secure the bridge with the sternum interior of the first leg and the second aperture receives a fixation device therethrough that engages the sternum at the second side of the opening to secure the bridge with the sternum interior of the second leg;
the second implant, when positioned in the insertion shape with the bridge in the insertion form and the first leg and the second leg in the insertion position at the second distance, being adapted to secure with the sternum across the opening at a second location, whereby the first leg inserts into the sternum adjacent a first side of the opening, the second leg inserts into the sternum adjacent a second side of the opening, and the bridge spans the opening; and the second implant, upon a movement thereof from the insertion shape toward the natural shape with the bridge moving toward the natural form and the first leg and the second leg moving toward the natural position, being adapted to hold the opening in the sternum closed at the second location, whereby the first aperture receives a fixation device therethrough that engages the sternum at the first side of the opening to secure the bridge with the sternum interior of the first leg and the second aperture receives a fixation device therethrough that engages the sternum at the second side of the opening to secure the bridge with the sternum interior of the second leg.

23. The sternal closure system of claim 22, wherein:

the bridge of the first implant moving toward the natural form and the first leg and the second leg moving toward the natural position facilitates an engagement of the first leg with the sternum at the first side of the opening and the second leg with the sternum at the second side of the opening and a compression of the sternum at the first location that holds the opening closed; and the bridge of the second implant moving toward the natural form and the first leg and the second leg moving toward the natural position facilitates an engagement of the first leg with the sternum at the first side of the opening and the second leg with the sternum at the second side of the opening and a compression of the sternum at the second location that holds the opening closed.

24. The sternal closure system of claim 22, wherein the bridge of the first and second implants includes at the central axis a groove, whereby the groove reduces a cross-section of the bridge and facilitates a cutting of the bridge that re-opens the opening in the sternum.

25. A method for a sternal closure system adapted for closing an opening in a sternum of a thoracic wall, comprising:

providing an implant moveable between a natural shape and an insertion shape, the implant comprising a bridge having a length, a first leg extending from the bridge, and a second leg extending from the bridge;

constraining the implant in the insertion shape;

providing a first plate including an aperture therethrough;

providing a second plate including an aperture therethrough;

securing a first plate with the sternum adjacent a first side of the opening, securing a second plate with the sternum adjacent a second side of the opening, whereby the aperture of the first plate and the aperture of the second plate are aligned and separated across the opening by a distance substantially equal to a distance between the first leg and the second leg when the implant resides in the insertion shape;

inserting the first leg of the implant through the aperture of the first plate into the sternum;

inserting the second leg of the implant through the aperture of the second plate into the sternum, whereby the bridge spans the opening;

releasing the implant whereby, upon a movement of the implant from the insertion shape toward the natural shape, the implant holds the opening in the sternum closed while the first leg engages the first plate and the second leg engages the second plate such that the implant interconnects the first plate and the second plate.

26. A method for a sternal closure system adapted for closing an opening in a sternum of a thoracic wall, comprising:

providing a first implant and a second implant moveable between a natural shape and an insertion shape, the first implant and the second implant, comprising:

a bridge having a length and with a first end, a second end, and a central axis therebetween, a first leg extending from the bridge at the first end, a second leg extending from the bridge at the second end; and the bridge including a first aperture therethrough between the central axis and the first leg and a second aperture therethrough between the central axis and the second leg;

constraining the first implant and the second implant in the insertion shape;

inserting the first leg of the first implant into the sternum adjacent a first side of the opening;

inserting the second leg of the first implant into the sternum adjacent a second side of the opening, whereby the bridge spans the opening at a first location;

releasing the first implant whereby, upon a movement of the first implant from the insertion shape toward the natural shape, the first leg engages with the sternum at the first side of the opening and the second leg engages with the sternum at the second side of the opening, further whereby the first implant compresses the sternum at the first location thereby holding the opening closed;

inserting a fixation device through the first aperture of the bridge for the first implant and into the sternum at the first side of the opening thereby securing the bridge with the sternum interior of the first leg;

inserting a fixation device through the second aperture of the bridge for the first implant and into the sternum at the second side of the opening thereby securing the bridge with the sternum interior of the second leg;

inserting the first leg of the second implant into the sternum adjacent a first side of the opening;

inserting the second leg of the second implant into the sternum adjacent a second side of the opening, whereby the bridge spans the opening at a second location;

releasing the second implant whereby, upon a movement of the second implant from the insertion shape toward the natural shape, the first leg engages with the sternum at the first side of the opening and the second leg engages with the sternum at the second side of the opening, further whereby the second implant compresses the sternum at the second location thereby holding the opening closed;

inserting a fixation device through the first aperture of the bridge for the second implant and into the sternum at the first side of the opening thereby securing the bridge with the sternum interior of the first leg;

inserting a fixation device through the second aperture of the bridge for the second implant and into the sternum at the second side of the opening thereby securing the bridge with the sternum interior of the second leg.

* * * * *